(12) United States Patent
Borrelli

(10) Patent No.: US 9,023,321 B2
(45) Date of Patent: May 5, 2015

(54) METHODS FOR PRODUCING MICROBUBBLES

(75) Inventor: Michael J. Borrelli, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 643 days.

(21) Appl. No.: 12/867,772

(22) PCT Filed: Mar. 20, 2009

(86) PCT No.: PCT/US2009/037851
§ 371 (c)(1),
(2), (4) Date: Nov. 1, 2010

(87) PCT Pub. No.: WO2009/117688
PCT Pub. Date: Sep. 24, 2009

(65) Prior Publication Data
US 2011/0044903 A1    Feb. 24, 2011

Related U.S. Application Data

(60) Provisional application No. 61/038,502, filed on Mar. 21, 2008.

(51) Int. Cl.
*A61K 49/22* (2006.01)

(52) U.S. Cl.
CPC .................................. *A61K 49/223* (2013.01)

(58) Field of Classification Search
None
See application file for complete search history.

(56) References Cited

U.S. PATENT DOCUMENTS

| | | | |
|---|---|---|---|
| 4,586,512 A | 5/1986 | Do-huu et al. | |
| 4,620,546 A | 11/1986 | Aida et al. | |
| 4,658,828 A | 4/1987 | Dory | |
| 4,774,958 A * | 10/1988 | Feinstein | 424/9.52 |
| 5,695,740 A | 12/1997 | Porter | |
| 5,980,950 A | 11/1999 | Porter | |
| 6,716,412 B2 | 4/2004 | Unger | |
| 7,025,726 B2 * | 4/2006 | Porter et al. | 600/458 |
| 7,115,583 B2 | 10/2006 | Porter et al. | |
| 2001/0031243 A1 | 10/2001 | Unger | |
| 2003/0044355 A1 | 3/2003 | Schutt | |
| 2003/0187371 A1 | 10/2003 | Vortman et al. | |
| 2007/0161902 A1 | 7/2007 | Dan | |
| 2011/0044903 A1 | 2/2011 | Borrelli | |

FOREIGN PATENT DOCUMENTS

| | | |
|---|---|---|
| EP | 0324938 A1 | 12/1988 |
| EP | 0 324 938 B1 | 11/1993 |
| WO | 03/026611 A2 | 4/2003 |
| WO | 2009117688 A2 | 9/2009 |
| WO | 2010/048623 A9 | 4/2010 |
| WO | 2010/084060 A1 | 7/2010 |
| WO | 2014/052311 A1 | 4/2014 |

OTHER PUBLICATIONS

Wong et al. In vivo study of microbubbles as an MR susceptibility contrast agent. 2004 Magn. Reson. Med. 52: 445-452.*
Ammi et al. Determining thresholds for contrast agent collapse. 2004 Proc. IEEE Ultrason. Symp. 1: 346-349.*
Alexandrov et al., "Ultrasound-enhanced systemic thrombolysis for acute ischemic stroke", New England Journal of Medicine, 2004, pp. 2170-2178, vol. 351.
Ammi et al., "Ultrasonic contrast agent shell rupture detected by inertial cavitation and rebound signals" IEEE Transactions Ultrasonics, Ferroelectrics and Frequency Control, 2006, pp. 126-136, vol. 53.
Bachmann et al., "Targeting mucosal addressin cellular adhesion molecule (MAdCAM)-1 to noninvasively image experimental Crohn's disease", Gastroenterology, 2006, pp. 8-16, vol. 130.
Bommannan et al., "Sonophoresis. I. The use of high-frequency ultrasound to enhance transdermal drug delivery", Pharmaceutical Research, 1992, pp. 559-564, vol. 9.
Borden et al., Influence of lipid shell physicochemical properties on ultrasound-induced microbubble destruction IEEE Transactions Ultrasonics, Ferroelectrics and Frequency Control, 2005, pp. 1992-2002, vol. 52.
Borrelli et al., "Ultrasonically induced morphological changes in the mammalian neonatal spinal cord", Ultrasound in Medicine and Biology, 1986, pp. 285-295, vol. 12.
Culp et al., "Microbubble potentiated ultrasound as a method of declotting thrombosed dialysis grafts: experimental study in dogs", Cardiovasc Intervent Radiol, 2001, pp. 407-412, vol. 24.
Daffertshofer et al., "Transcranial low-frequency ultrasound-mediated thrombolysis in brain ischemia: increased risk of hemorrhage with combined ultrasound and tissue plasminogen activator: results of a phase II clinical trial", Stroke, (2005), pp. 1441-1446, vol. 36.
Dayton et al., Optical and acoustical observations of the effects of ultrasound on contrast agents. IEEE Transactions Ultrasonics, Ferroelectrics and Frequency Control, 1999, pp. 220-232, vol. 46.
Eggers et al., "Sonothrombolysis in acute ischemic stroke for patients ineligible for rt-PA", Neurology, 2005, pp. 1052-1054, vol. 64.
Grinstaff et al. "Air-filled proteinaceous microbubbles: Synthesis of anecho-contrast agent", Proceedings of the National Academy of Sciences USA, 1991, pp. 7708-7710, vol. 88.

(Continued)

*Primary Examiner* — Michael G Hartley
*Assistant Examiner* — Jennifer Lamberski
(74) *Attorney, Agent, or Firm* — Polsinelli PC

(57) ABSTRACT

The present invention provides methods for the preparation of gas-filled microbubbles, and methods of using for therapeutic and/or diagnostic applications. In particular, the methods of the invention allow for the preparation of gas-filled microbubbles having narrow size distributions and defined ultrasonic properties.

16 Claims, 7 Drawing Sheets

(56) References Cited

OTHER PUBLICATIONS

Haak, et al., "Detection of Microbubble Ultrasound Contrast Agent Destruction Applied to Definity", Proceedings of the International Congress on Ultrasonics, 2007 Paper No. 1719.

Holland et al., "Ultrasound-enhanced tissue plasminogen activator thrombolysis in an in vitro porcine clot model", Thrombosis Research, 2008, pp. 663-673, vol. 121.

Kheirolomoom et al., "Acoustically-active microbubbles conjugated to liposomes: characterization of a proposed drug delivery vehicle", Journal of Controlled Release, 2007, pp. 275-284, vol. 118.

Kinoshita et al., "Intracellular Delivery of Bak BH3 peptide by microbubble-enhanced ultrasound", Pharmaceutical Research, 2005, pp. 716-720, vol. 22.

Lai et al., "Quantitative relations of acoustic inertial cavitation with sonoporation and cell viability", Ultrasound in Medicine and Biology, 2006, pp. 1931-1941, vol. 32.

Lavon et al., "Bubble growth within the skin by rectified diffusion might play a significant role in sonophoresis", Journal of Controlled Release, 2007, pp. 246-255, vol. 117, No. 2.

Lepock et al., "Influence of transition rates and scan rate on kinetic simulations of differential scanning calorimetry profiles of reversible and irreversible protein denaturation", Biochemistry, 1992, pp. 12706-12712, vol. 31.

Miller, et al., "Influence of contrast agent dose and ultrasound exposure on cardiomyocyte injury induced by myocardial contrast echocardiography in rats", Radiology, 2005, pp. 137-143, vol. 237.

Mitragotri et al, "Determination of threshold energy dose for ultrasound-induced transdermal drug transport", Journal of Controlled Release, 2000, pp. 41-52, vol. 63.

Ohta et al., "Gene transduction by sonoporation" Development, Growth and Differentiation, 2008, pp. 517-520, vol. 50.

Porter et al., "Effectiveness of Transcranial and Transthoracic Ultrasound and Microbubbles in Dissolving Intravascular Thrombi", Journal of Ultrasound in Medicine, 2001, pp. 1313-1325, vol. 20.

Shohet et al., "Echocardiographic destruction of albumin microbubbles directs gene delivery to the myocardium", Circulation, 2000, pp. 2554-2556, vol. 101.

Tiukinhoy-Laing, et al, "Ultrasound-facilitated thrombolysis using tissue-plasminogen activator-loaded echogenic liposomes", Thrombosis Research, 2007, pp. 777-784, vol. 119.

Zachary et al., "Vascular lesions and S-Thrombomodulin concentrations from auricular arteries of rabbits infused with microbubble contrast agent and exposed to pulsed ultrasound" Ultrasound in Medicine and Biology, 2006, pp. 1781-1791, vol. 32.

International Search Report for PCT/US09/37851 dated Jun. 16, 2009; 3 pages.

International Search Report and Written Opinion dated Jul. 20, 2011 from related International Patent Application No. PCT/US2013/61396, dated Feb. 6, 2014; 11 pgs.

Rajalakshmi et al., "A Review on Ultrasonic Microbubbles", International Journal of Pharmacy, 2011, pp. 1-12; vol. 1, No. 1.

* cited by examiner

METHODS FOR PRODUCING MICROBUBBLES

STATEMENT REGARDING FEDERALLY SPONSORED RESEARCH

This invention was made with government support under Grant Number R01-CA099178 awarded by the National Cancer Institute at the National Institutes of Health. The government has certain rights in the invention.

FIELD OF THE INVENTION

The present invention relates to methods for preparing gas-filled microbubbles for therapeutic and/or diagnostic uses.

BACKGROUND OF THE INVENTION

Microbubbles have been used in biomedical applications as ultrasound contrast agents, blood substitutes, agents for ultrasonic-induced lysis of stroke-causing thrombi (sonothrombolysis), and drug and gene delivery vehicles. Many of these applications require the microbubbles to be sufficiently stable so as to circulate in the blood for a long enough period of time to reach the intended target site. Furthermore, many microbubble preparations behave non-uniformly with respect to an insonating ultrasonic field. These preparations often contain a non-homogenous mixture of microbubbles with diameters ranging from 0.5 µm to 6.0 µm. Protocols that enable one to produce and tailor microbubbles to perform in a more defined and controlled manner, e.g. to lyse only in response to a specific ultrasound intensity and frequency, to withstand rapid acoustic-induced collapse when administered, and to be stored for protracted periods of time until their use are desired. Hence, there is a need for methods to manufacture microbubble preparations that are more homogenous with respect to size distribution, acoustic collapse threshold, resonant frequency, and other physical or acoustical properties.

SUMMARY OF THE INVENTION

Among the various aspects of the present invention is the provision of a method for preparing a plurality of fluorocarbon gas-filled microbubbles having a narrow size distribution and a defined acoustic performance. In particular, at least 80% of the microbubbles have diameters within about 10% of a selected mean diameter, with the mean diameter ranging from about 1 to 6 microns. The plurality of microbubbles has an average, single microbubble acoustic collapse threshold about 0.3-30 MPa. The method comprises saturating a solution comprising serum albumin and dextrose with the perfluorocarbon gas. The method further comprises delivering a first round of ultrasound energy within the solution, and delivering a second round of ultrasound energy outside the solution.

Another aspect of the present invention encompasses a method for preparing a plurality of fluorocarbon gas-filled microbubbles having an average single microbubble acoustic collapse threshold of about 0.3-30 MPa, and wherein at least 90% of the microbubbles have diameters within about 10% of a selected mean diameter, with the mean diameter ranging from about 0.5 to about 1 micron. The method comprises saturating a solution comprising serum albumin and dextrose with the perfluorocarbon gas. The method further comprises delivering ultrasound energy to the solution at a power level of about 400-500 W and a frequency of about 20 kHz.

Still another aspect of the present invention provides a method for treating a subject in need thereof. The method comprising administering a plurality of microbubbles prepared according to one of the methods of the invention to the subject. The method further comprises applying ultrasound energy to the subject.

A further aspect of the invention encompasses a microbubble prepared by a method of the invention.

Other aspects and features of the invention are detailed below.

DETAILED DESCRIPTION OF THE INVENTION

Figure 1:
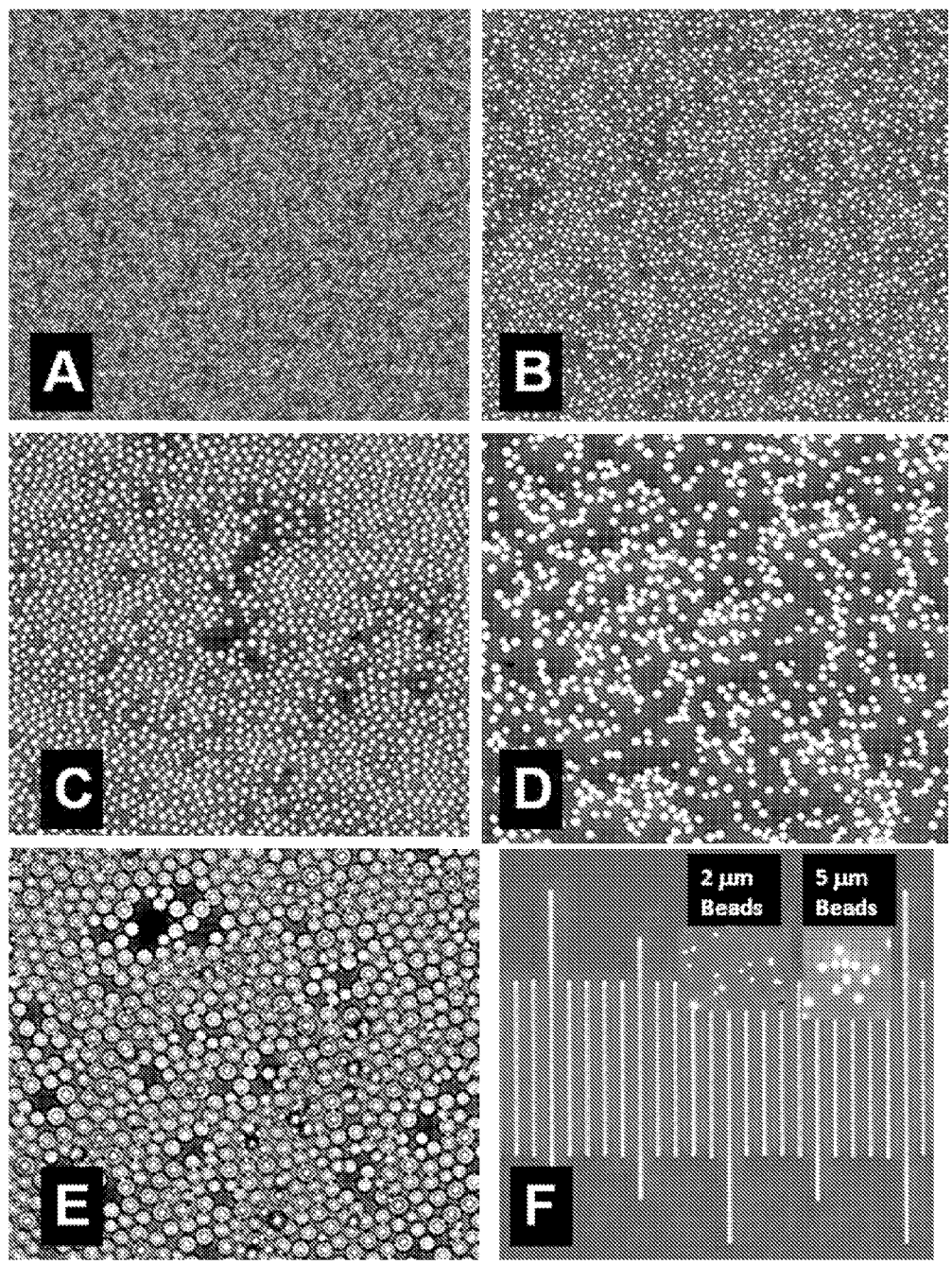
FIG. 1 presents images of microbubble preparations having narrow size distributions prepared by methods of the invention. (A) 1.0 µm average diameter; (B) 3.0 µm average diameter; (C) 3.0 µm average diameter; (D) 4.5 µm average diameter; (E) 6.5 µm average diameter; (F) Size standards: 2 µm and 5 µm latex beads and a scale bar.

The present invention provides methods for preparing gas-filled microbubbles having more homogeneous and narrow size distributions and defined acoustic properties. As detailed in the Examples, methods have been discovered for the production of microbubbles having narrow size distributions, distinct shell properties (e.g., thickness, strength, elasticity), and defined acoustic properties. Accordingly, microbubbles with thicker or stronger shells may function as long-lived contrast agents over a wide range of ultrasonic intensities. Alternatively, microbubbles with thinner or weaker shells may produce more inertial cavitational activity in response to an ultrasonic field and may better facilitate sonothrombolysis or sonoporation. Moreover, the microbubbles of the invention may further comprise a biological agent such that the microbubbles may be used in therapeutic and/or diagnostic applications.

(I) Methods for Preparing Microbubbles

One aspect of the present invention provides methods for preparing microbubbles that have narrow size distributions and defined physical and/or acoustical properties. In general, the methods comprise sonicating a solution comprising a protein, a saccharide, and a gas, wherein changes in the concentration of the protein and/or the saccharide, and/or changes the intensity or duration of the sonication step(s) affects the size and/or acoustic properties of the resultant microbubbles. As used herein, a microbubble comprises a gaseous interior that is surrounded by an outer shell comprising protein and saccharide.

(a) Preparing the Solution

The first step of the process of the invention comprises forming a solution comprising a protein and a saccharide and then saturating the solution with the gas.

(i) Protein

The solution may comprise a variety of different proteins. The protein may be a single protein or a mixture of proteins. In general, the protein may be any nontoxic protein. The protein may be naturally occurring, synthetic, or recombinant. In some embodiments, the protein may be a pharmaceutically acceptable protein. Examples of suitable proteins include, without limit, natural blood proteins, serum proteins, albumin, gamma globulin, hemoglobin, gelatin, collagen, or combinations thereof. In preferred embodiments, the protein may be a serum albumin. The serum albumin may be bovine, murine, rat, rabbit, and/or human. In one preferred embodiment, the protein may be bovine serum albumin. In another preferred embodiment, the protein may be human serum albumin.

The concentration of the protein in the protein-saccharide solution can and will vary depending upon the size and/or the desired physical characteristics of the microbubble to be made. In general, the concentration of the protein in the solution will be less the about 20% (w/v). In one embodiment, the concentration of the protein in the solution may range from about 15% to about 20% (w/v). In another embodiment, the concentration of the protein in the solution may range from about 10% to about 15% (w/v). In still another embodiment, the concentration of the protein in the solution may range from about 5% to about 10% (w/v). In yet a further embodiment, the concentration of the protein in the solution may range from about 0.1% to about 5% (w/v). In a preferred embodiment, the concentration of the protein in the solution may range from about 1% to about 15% (w/v). In an exemplary embodiment, the concentration of the protein in the solution may range from about 1% to about 6% (w/v).

(ii) Saccharide

Numerous saccharides are suitable for use in the invention. In some embodiments, the saccharide may be pharmaceutically acceptable. The saccharide may be a monosaccharide, a disaccharide, a polysaccharide, or mixtures thereof. Non-limiting examples of suitable monosaccharides include a pentose such as fructose, a hexose such as glucose (i.e., D-glucose or dextrose), galactose, and the like. Other suitable monosaccharides include sugar alcohols such as xylitol, mannitol, sorbitol, and the like. Suitable disaccharides include, without limit, sucrose, lactose, maltose, and the like. Non-limiting examples of suitable polysaccharides include starch, amylose, cellulose, dextran, and the like. In an exemplary embodiment, the saccharide may be dextrose.

The concentration of the saccharide in the protein-saccharide solution can and will vary depending upon the size and/or the desired physical characteristics of the microbubble to be made. In general, the concentration of the saccharide in the solution will be less the about 20% (w/v). In one embodiment, the concentration of the saccharide in the solution may range from about 15% to about 20% (w/v). In another embodiment, the concentration of the saccharide in the solution may range from about 10% to about 15% (w/v). In still another embodiment, the concentration of the saccharide in the solution may range from about 5% to about 10% (w/v). In yet a further embodiment, the concentration of the saccharide in the solution may range from about 0.1% to about 5% (w/v). In a preferred embodiment, the concentration of the saccharide in the solution may range from about 1% to about 15% (w/v). In an exemplary, the concentration of the saccharide in the solution may range from about 3% to about 12% (w/v).

Typically, the solution comprising the protein and the saccharide is prepared by mixing a protein stock solution with a saccharide stock solution. The protein and saccharide solutions may be mixed in different volume-to-volume ratios. The protein and saccharide solutions may be mixed in a volume-to-volume ratio of protein solution to saccharide solution ranging from about 2:1 to about 1:10. In various embodiments, the protein and saccharide solutions may be mixed in a volume-to-volume ratio of protein solution to saccharide solution of: 2:1, 1.5:1, 1:1, 1:2, 1:3, 1:4, 1:5, 1:6, 1:7, 1:8, 1:9, or 1:10.

(iii) Gas

The protein-saccharide solution is saturated with a gas such that upon sonication gas-filled microbubbles may be formed. A variety of chemical compounds are suitable for use as the gas in the invention. In general, the chemical compound will be a gas at body temperature and be nontoxic. In some embodiments, the gas may be pharmacologically acceptable. In certain embodiments, the gas may be inert. Non-limiting examples of suitable gasses include air, carbon dioxide, nitrogen, oxygen, nitrous oxide, helium, argon, nitric oxide, xenon, a perfluorocarbon gas, or mixtures thereof. In preferred embodiments, the gas may be a fluorocarbon gas such as tetrafluoromethane, hexafluoroethane, octafluoropropane, decafluorobutane, or perfluoro-isobutane. In an exemplary embodiment, the gas may be decafluorobutane.

Typically, the gas is added to and mixed with the protein-saccharide solution prior to application of the ultrasound energy. The amount of gas added to the protein-saccharide solution can and will vary. In general, the amount of gas added to the solution may range from about 20% to about 220% (volume-to-volume). The gas may be applied to or layered over the surface of the protein-saccharide solution. The gas may be dissolved and/or interspersed into the solution by hand agitation, rotation, shaking, inversion mixing, rolling mixing, vortex mixing, or combinations thereof. In preferred embodiments, the gas may be mixed with the protein-saccharide solution by vortexing. The vortex mixing may be constant or it may be discontinuous. The speed of the vortex mixing can and will vary. In some embodiments, the vortexing speed may be maximal. In other embodiments, the vortexing speed may be less than maximal. In general, a gas-saturated protein-saccharide solution has a translucent opaque appearance.

(b) Delivering Ultrasound Energy

The methods further comprise delivering ultrasound energy to the gas saturated protein-saccharide solution. The ultrasound energy may be provided by a Fisher model 500 sonicator. Alternatively, the ultrasound energy may be provided by any commercially available sonicator or sonic disruptor provided the sonicator sonic disruptor is calibrated to deliver the same level of power as a Fisher model 500 sonicator, as detailed in Example 3 and plotted in FIG. 2.

Typically, the ultrasound energy is applied via a sonic probe (or horn) attached to the sonicator or sonic disruptor. The shape and diameter of the sonic probe may vary, depending upon, for example, the volume of solution to be sonicated. In one embodiment, the sonic probe may have a flat tip with a diameter of 1.1 cm. In another embodiment, the sonic probe may have a flat tip with a diameter of 1.9 cm. Those of skill in the art will appreciate that the sonic probe may have other shapes and/or sizes. For example, larger volumes of the protein-saccharide solution generally will require proportionately larger diameter sonic probes to produce the microbubbles.

Typically, the ultrasonic mixing will be performed at 20 kHz and at a variety of different power levels. In general, the power level may range from about 100 W to about 500 W. In certain embodiments, the power level may range from about 100 W to about 200 W, from about 200 W to about 300 W, from about 300 W to about 400 W, or from about 400 W to about 500 W, from about 100 W to about 300 W, from about 200 W to about 500 W, or from about 300 W to about 500 W.

The ultrasound energy may be applied to the protein-saccharide-gas solution for a period of time that ranges from about 1 second to about 200 seconds. In some embodiments, the duration of the time may range from about 1 second to about 5 seconds, from about 5 seconds to about 20 seconds, from about 20 seconds to about 40 seconds, from about 40 seconds to about 80 seconds, from about 80 seconds to about 120 seconds, or from about 120 seconds to about 200 seconds.

Microbubbles may be prepared using a one-step, a two-step, or a multi-step sonication protocol. In general, the two-step sonication protocol may be used to prepare microbubbles having an average diameter of about 1.0, 2.0, 3.0, 4.0, and 5-6 microns; and the one-step sonication protocol may be used to prepare microbubbles having an average diameter of about 1.0 micron or less. In general, protocols using more than two sonication steps may be used to increase the acoustic stability (resistance to ultrasonic lysis) for microbubbles larger than 1.0 µm, e.g. to produce microbubble preparations with average single microbubble collapse thresholds greater than 12-15 MPa.

The one-step sonication process comprises delivering ultrasound energy outside the solution by placing the tip of the sonic probe at the surface of the solution or positioning the tip of the sonic probe no more than about 5 mm above the surface of the solution.

The two-step sonication process comprises (1) delivering a first round of ultrasound energy within the solution by immersing the sonic probe in the solution; and (2) delivering a second round of ultrasound energy outside the solution by placing the tip of the sonic probe at the surface of the solution or positioning the tip of the sonic probe no more than about 5 mm above the surface of the solution.

The multi-step sonication process comprises (1) delivering a first round of ultrasound energy within the solution by immersing the sonic probe in the solution; (2) delivering a second round of ultrasound energy outside the solution by placing the tip of the sonic probe at the surface of the solution or positioning the tip of the sonic probe no more than about 5 mm above the surface of the solution; (3) delivering subsequent rounds of ultrasound energy outside the solution as detailed in (2).

In general, the vessel containing the protein-saccharide solution is flushed with gas prior to each sonication step.

(i) Delivering Ultrasound Energy within the Solution

The two-step (and the multi-step) sonication process comprises a first step of delivering ultrasound energy within the solution. In general, ultrasound energy is delivered within the solution by immersing the tip of the sonic probe (horn) into the solution. The relative depth of the sonic probe tip can and will vary depending upon the volume of the solution to be ultrasonically mixed and the size of the containment vessel. In a preferred embodiment, the sonic probe tip may be immersed into the gas-saturated protein-saccharide solution to a depth about one-half of the distance from the surface of the solution to the bottom of the vessel. Stated another way, the sonic probe tip may be immersed in the solution and positioned at the midpoint of the solution volume.

In another embodiment, the sonic probe tip may be immersed into the solution to a depth up to one-third of the distance from the surface of the solution to the bottom of the vessel. In a further embodiment, the sonic probe tip may be immersed into the solution to a depth up to one-quarter of the distance from the surface of the solution to the bottom of the vessel. In still another embodiment, the sonic probe tip may be immersed into the solution to a depth up to one-tenth of the distance from the surface of the solution to the bottom of the vessel. In further embodiments, the sonic probe tip may be immersed between 0.05 cm and 10 cm below the surface of the solution. In various embodiments, the sonic probe tip may be immersed between 0.02 cm and 4 cm, between 0.1 cm and 10 cm, between 0.5 cm and 10 cm, between 1 cm and 10 cm, between 2 cm and 8 cm, between 3 cm and 7 cm, or between 4 cm and 6 cm below the surface of the solution.

(ii) Delivering Ultrasound Energy Outside the Solution

The one-step sonication process, the second step of the two-step sonication process, and all the steps after the first step of the multi-step sonication processes all comprise delivering the ultrasound energy outside the solution. In general, ultrasound energy is delivered outside the solution by positioning the tip of the sonic probe at the surface of the solution or positioning the sonic probe tip above the surface of the solution. The position of the sonic probe tip above the surface of the solution can and will vary, depending upon the volume of the solution to be ultrasonically mixed and the size of the containment vessel, for example.

In one embodiment, the tip of the sonic probe may be placed at a location above the surface of the solution that ranges from about 0.5% to about 2% of the distance between the surface of the solution and the bottom of the containment vessel. In another embodiment, the tip of the sonic probe may be placed at a location above the surface of the solution that ranges from about 1% to about 5% of the distance between the surface of the solution and the bottom of the containment vessel. In yet another embodiment, the tip of the sonic probe may be placed at a location above the surface of the solution that ranges from about 5% to about 20% of the distance between the surface of the solution and the bottom of the containment vessel. In other embodiments, the tip of sonic probe may be placed from about 1 mm to about 10 mm above the surface of solution. In various embodiments, the sonic probe tip may be placed from about 1 mm to about 3 mm, from about 3 to about 6 mm, or from about 6 to about 10 mm. In preferred embodiments, the sonic probe tip may be placed from about 0.1 mm to about 5 mm, more preferably from about 1 mm to about 3 mm, or even more preferably about 1 mm to about 2 mm above the surface of solution. In one exemplary embodiment, the sonic probe tip may be placed no more than about 2 mm above the surface of the solution. In another exemplary embodiment, the sonic probe tip may be placed no more than about 5 mm above the surface of the solution.

(c) Exemplary Embodiments

Microbubbles having a narrow size distribution around a selected mean diameter and defined acoustic properties may be prepared by 1) varying the concentration of the protein and/or saccharide in the solution; 2) varying the intensity of the ultrasound energy delivered; and/or 3) varying the duration of the sonication step or step(s). In exemplary embodiments, the protein is serum albumin, the saccharide is dextrose, and the gas is decafluorobutane. Table A lists various protocols for producing decafluorobutane-filled albumin-dextrose microbubbles of a particular mean diameter. The protocols utilize 16 ml of solution, a 1.9 cm diameter sonic probe, and a Fisher Model 500 sonicator. Those of skill in the art appreciate that the volumes of solution may be scaled up or down as needed. In general, the protocols listed in Table A are used as template (starting point) protocols for producing new protocols that yield microbubbles with different size distributions and/or acoustic properties. The parameters of the protocols in Table A may be varied according to the schemes described below to develop new protocols with desired microbubble size distributions and acoustic properties.

TABLE A

Microbubble Preparation Protocols.

| Diameter | Protocol | Serum Albumin (%) | Dextrose (%) | Sonication Step 1 | Sonication Step 2 |
|---|---|---|---|---|---|
| 1.0 µm | A | 1.25% | 3.75% | 450 W 70-80 sec | None |
|  | B | 1.25% | 3.75% | 150 W 20-30 sec | 400-450 W 70 sec |
| 2.0 µm | A | 1.25% | 3.75% | 125 W 30 sec | 375 W 45 sec |
|  | B | 3.75% | 11.25% | 250 W 25 sec | 300 W 20 sec |
| 3.0 µm | A | 1.65% | 10.0% | 250 W 30 sec | 450 W 20 sec |
|  | B | 5.0% | 10.0% | 250 W 30 sec | 450 W 20 sec |
|  | C | 5.0% | 10.0% | 250 W 40 sec | 450 W 30 sec |
| 4.0 µm | A | 1.25% | 3.75% | 250 W 30 sec | 350 W 40 sec |
|  | B | 5.0% | 10.0% | 300 W 25 sec | 250 W 40 sec |
| 5-6 µm | A | 1.25% | 3.75% | 250 W 35 sec | 250 W 45 sec |
|  | B | 5.0% | 10.0% | 300 W 25 sec | 200 W 30 sec |

In general, increasing the power of the first step/round of ultrasound energy increases the average diameter of the plurality of microbubbles; increasing the power of the step/second round of ultrasound energy decreases the average diameter of the plurality of microbubbles; increasing the concentration of the serum albumin increases the size stability of microbubbles having mean diameters greater than about 2 microns; increasing the concentration of the serum albumin increases the acoustic collapse threshold among microbubbles having the same mean diameter; increasing the power level or duration of the first round of ultrasound energy increases the acoustic collapse threshold among microbubbles having the same mean diameter; and increasing the power level of the second round of ultrasound energy increases the acoustic collapse threshold among microbubbles having the same mean diameter.

(d) Treatment with Acidic Buffer

In some embodiments, the microbubbles may be treated with a buffer having an acidic pH. In general, the size stability, storage time (i.e., shelf life), and/or the acoustic stability of the microbubbles is increased by treatment with a buffer having a pH ranging from about 2 to about 7. In general, the lower the pH of the treatment buffer, the greater the stability afforded to the microbubbles. Non-limiting examples of suitable buffers include citrate buffers, succinate-based buffers, acetate buffers, phosphate buffered saline, PIPES, MES, and Tris maleate. In an exemplary embodiment, the buffer may be a citrate buffer and the pH of the buffer may be about 2, about 3, about 4, about 5, about 6, or about 7. In another exemplary embodiment, the buffer may be a citrate buffer and the pH of the buffer may be about 3, about 4, or about 5.

The duration of time during which the microbubbles are in contact with the acidic buffer can and will vary. In general, the duration of time the microbubbles are in contact with the acidic buffer will range from about 1 minute to about 6 hours. In some embodiments, the duration of time the microbubbles are in contact with the acidic buffer may be at least about 1, 5, 10, 15, 20, 30, 40, 50, or 60 minutes. In other embodiments, the duration of time the microbubbles are in contact with the acidic buffer may be at least about, 1, 2, 3, 4, 5, or 6 hours.

The microbubbles may be treated with the acidic buffer immediately after sonication and their preparation. Alternatively, the microbubbles may be treated with the acidic buffer after a period of time has elapsed after their preparation. The period of time may range from several minutes to several hours after their preparation. In still another embodiment, the microbubbles may be treated with acidic buffer while they are being size separated (see below). In a further embodiment, the microbubbles may be treated with acidic buffer after they have been size separated. In general, the magnitude of the changes in size stability, shelf life, and acoustic durability (resistance to ultrasonic lysis) will decrease with a longer time delay between microbubble production and treatment with buffers with pH levels lower than 7.4.

Treatment with the acidic buffer may increase the size stability, storage time (i.e., shelf life), and/or the acoustic stability of the microbubbles by at least about 1.5-fold, 2-fold, 3-fold, 4-fold, 5-fold, 6-fold, 7-fold, 8-fold, 9-fold, 10-fold, or more than 10-fold.

(e) Biological Agent

The method of the invention may be modified to permit introduction of at least one biological agent. "Biological agent" as used herein refers to an agent having pharmacological, therapeutic, and/or diagnostic effects on a subject. Examples of suitable biological agents include, without limit, contrast agents, pharmaceutically active agents, prodrugs, proteins, peptides, antibodies or fragments thereof, and nucleic acids.

The biological agent may be entrapped with the gas inside the microbubble. Alternatively, the biological agent may be associated with the protein-saccharide shell of the microbubble. In one embodiment, the biological agent may enmeshed in the shell via attachment to the protein and/or the saccharide. The attachment may be covalent or non-covalent or the biological agent. In another embodiment, the biological agent may be on the surface of the microbubble via covalent or non-covalent interactions with the components of the shell.

In one embodiment, the biological agent may be attached to the protein and/or the saccharide prior to microbubble formation. For example, the biological agent may be introduced into the saccharide solution, the protein solution, and/or the protein-saccharide solution. In another embodiment, the biological agent may be added to or mixed with the protein-saccharide-gas solution prior to application of the ultrasound energy. In yet another embodiment, the biological agent may be attached to an already formed microbubble. Stated another way, the microbubbles may be contacted with a biological agent after their formation and/or after their size separation.

Non-limiting examples of suitable contrast agents include iodinated contrast agents, metallic contrast agents, magnetic contrast agents, and radioisotope agents. In one embodiment, the biological agent may be an iodinated contrast agent, which may comprise an ionic or a non-ionic (i.e., organic) compound. In another embodiment, the biological agent may be a radioopaque metal ion, such as iodine, barium, bromine, or tungsten, and may be used as an x-ray contrast agent. In a further embodiment, the biological agent may be a paramagnetic gas, such as atmospheric air, which may contain paramagnetic ions such as $Mn^{+2}$, $Gd^{+2}$, $Fe^{+3}$; iron oxides or magnetite ($Fe_3O_4$) and may thus be used as a susceptibility contrast agent for magnetic resonance imaging (MRI). Additionally, the biological agent may be a gas from a quadrupolar nuclei, and may have potential for use as a Magnetic Resonance contrast agent. In yet another embodiment, the biological agent may be a radioisotope such as carbon-11, nitrogen-13, oxygen-15, fluorine-18, iridium-191, lutetium-177, iodine-131, technetium-99m, rubidium-82, strontium-82, yttrium-90, iodine-131, phosphorus-32, and actinium-225, and may be used for ultrasound imaging and/or positron emission tomography.

In another embodiment, the biological agent may be a pharmaceutically active agent. Pharmaceutically active agents include small organic molecules, peptides, proteins, enzymes, antibodies, and the like. In various embodiments, the pharmaceutically active agent may be an antineoplastic agent, such as a platinum compound (e.g., spiroplatin, cisplatin, and carboplatin), methotrexate, fluorouracil, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, arabinosyl, hydroxyurea, procarbazine, dacarbazine, or a mitotic inhibitor such as etoposide; a radiopharmaceutical such as radioactive iodine and/or a phosphorus product; a hormone such as progestin, estrogen, or antiestrogen; an anti-helmintic, antimalarial, and/or an antituberculosis drug; an immune serum, an antitoxin, and/or an antivenin; a rabies prophylaxis product; a bacterial vaccine; a viral vaccine; aminoglycoside; a respiratory product such as a xanthine derivative, theophylline, or aminophylline; a thyroid agent such as an iodine product or anti-thyroid agent; a cardiovascular product including a chelating agent, a mercurial diuretic, and/or a cardiac glycoside; glucagon; a blood product such as parenteral iron, hemin, hematoporphyrin, and/or their derivatives; a biological response modifier such as muramyldipeptide, muramyltripeptide, a microbial cell wall component, a lymphokine (e.g., bacterial endotoxin such as lipopolysaccharide, macrophage activation factor), a subunit of bacteria (such as Mycobacteria, Corynebacteria), or the synthetic dipeptide N-acetyl-muramyl-L-alanyl-D-isoglutamine; an anti-fungal agent such as ketoconazole, nystatin, griseofulvin, flucytosine (5-FC), miconazole, amphotericin B, ricin, cyclosporins, or β-lactam antibiotics (e.g., sulfazecin); a hormone such as growth hormone, melanocyte stimulating hormone, estradiol, beclomethasone dipropionate, betamethasone, betamethasone acetate, betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone terbutate, prednisone, triamcinolone, triamcinolone acetonide, triamcinolone diacetate, triamcinolone hexacetonide and fludrocortisone acetate, oxytocin, vassopressin, or their derivatives; a vitamin such as cyanocobalamin neinoic acid, a retinoid and/or a derivative such as retinol palmitate, or α-tocopherol; a peptide, such as manganese super oxide dimutase; an enzyme such as alkaline phosphatase; a fibrolytic enzyme such as tissue plasminogen activator (tPA); an anti-allergic agent such as amelexanox; an anti-coagulation agent such as phenprocoumon or heparin; a circulatory drug such as propranolol; a metabolic potentiator such as glutathione; an antitubercular such as para-aminosalicylic acid, isoniazid, capreomycin sulfate cycloserine, ethambutol hydrochloride ethionamide, pyrazinamide, rifampin, or streptomycin sulfate; an antiviral such as acyclovir, amantadine azidothymidine (AZT or Zidovudine), ribavirin and vidarabine monohydrate (adenine arabinoside, ara-A); an antianginal such as diltiazem, nifedipine, verapamil, erythrityl tetranitrate, isosorbide dinitrate, nitroglycerin (glyceryl trinitrate), or pentaerythritol tetranitrate; an anticoagulant such as phenprocoumon, heparin, or coumadin; an antibiotic such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin, including penicillin G, penicillin V, ticarcillin rifampin, or tetracycline; an anti-inflammatory such as difunisal, ibuprofen, indomethacin, meclofenamate, mefenamic acid, naproxen, oxyphenbutazone, phenylbutazone, piroxicam, sulindac, tolmetin, aspirin and salicylates (plus other non-steroidal anti-inflammatory drugs (NSAIDS) with antineoplastic activity); an antiprotozoan such as chloroquine, hydroxychloroquine, metronidazole, quinine, or meglumine antimonate; antirheumatics such as penicillamine; narcotics such as paregoric; an opiate such as codeine, heroin, methadone, morphine, or opium; a cardiac glycoside such as deslanoside, digitoxin, digoxin, digitalin, or digitalis; a neuromuscular blocker such as atracurium besylate, gallamine triethiodide, hexafluorenium bromide, metocurine iodide, pancuronium bromide, succinylcholine chloride (suxamethonium chloride), tubocurarine chloride, or vecuronium bromide; a sedative such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam, or triazolam; a local anesthetic such as bupivacaine hydrochloride, chloroprocaine hydrochloride, etidocaine hydrochloride, lidocaine hydrochloride, mepivacaine hydrochloride, procaine hydrochloride, or tetracaine hydrochloride; a general anesthetic such as droperidol, etomidate, fentanyl citrate with droperidol, ketamine hydrochloride, methohexital sodium, or thiopental sodium; an monoclonal antibody or fragment thereof; or a radioactive particle or ion such as strontium, iodide rhenium, or yttrium.

In further embodiments, the biological agent may be a nucleic acid such as RNA, DNA, and combinations thereof, of either natural or synthetic origin, including recombinant RNA and DNA, antisense RNA and DNA, and silencing RNA (siRNA). Types of nucleic acids that may be used include, for example, genes carried on expression vectors such as plasmids, phagemids, cosmids, yeast artificial chromosomes (YACs), viral gene therapy vectors (e.g. nonreplicating adenoviruses, adeno-associated viruses, retro-viruses, etc.), defective or "helper" viruses, antigene nucleic acids, both single and double stranded RNA and DNA and analogs thereof, such as phosphorothioate, phosphoroamidate, and phosphorodithioate oligodeoxynucleotides. Additionally, the nucleic acid may be combined, for example, with proteins or polymers. In still other embodiments, the biological agent may be a liposome. The liposome may be attached to the microbubble and carry pharmaceutically active agents, nucleic acids, etc., that may be released by the microbubble as it oscillates and/or implodes in response to an acoustic field.

In yet further embodiments, the biological agent may be a prodrug. Prodrugs may include inactive drug precursors which, when exposed to high temperature, metabolizing enzymes, cavitation and/or pressure, in the presence of oxygen or otherwise, or when released from the microbubble and/or attached liposomes, will form pharmaceutically active agents. Such prodrugs may be activated from, or released from, gas-filled microbubbles upon the application of ultrasound or radiofrequency microwave energy to the prodrug-containing microbubble with the resultant cavitation, heating, pressure, and/or release from the microbubble. Prodrugs may comprise inactive forms of the active agent wherein a chemical group is present on the prodrug that renders it inactive and/or confers solubility or some other property to the drug. In this form, the prodrugs may generally be inactive, but once the chemical group has been cleaved from the prodrug, by heat, cavitation, pressure, and/or by enzymes in the surrounding environment or otherwise, the pharmaceutically active agent may be generated. Such prodrugs comprise a wide variety of agents bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and β-glucoside. Prodrugs may be designed to contain reversible derivatives that are utilized as modifiers of duration of activity to provide, prolong or depot action effects. For example, nicotinic acid may be modified with dextran and carboxymethyldextran esters, streptomycin with alginic acid salt, dihydrostreptomycin with pamoate salt, cytarabine (ara-C) with 5'-adamantoate ester, ara-adenosine (ara-A) with 5-palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl)ethers, and cycloguanil with pamoate salt. In this form, a depot or reservoir of long-acting drug may be released in vivo from the gaseous precursor-filled prodrug bearing microbubbles.

The particular chemical structure of the biological agent may be selected or modified to achieve desired solubility such that the agent may be encapsulated within the internal space of the microbubble, attached to the shell, or enmeshed in the shell. The surface-bound biological agent may bear one or more acyl chains such that, when the microbubble is ruptured via cavitation, the acylated agent may then leave the surface and/or the agent may be cleaved from the acyl chains chemical group. Similarly, other agents may be formulated with a hydrophobic group that is aromatic or sterol in structure to incorporate into the surface of the microbubble. The biological agent may be encapsulated within a liposome that is attached to the microbubble to be released when the liposome is ruptured or otherwise permeabilized by the microbubble as the microbubble oscillates and/or implodes in response to acoustic pressure and/or intensity.

The biological agent also may be a nanoparticle (0.5 to 800 nm in diameter) with a biologically or medically relevant function. Such nanoparticles may be attached to the microbubbles using one of many different cross-linking or bio-conjugation chemistries, and one or many nanoparticles may be attached to each microbubble. The nanoparticles may be comprised of ferric iron (magnetic), carbon (carbon nanotubes, carbon buckeyballs, carbon nanofibers, etc.), quantum dots, plastic, cobalt, carbon-coated cobalt, and any other particle that is considered a nanoparticle, including naturally occurring viruses (e.g. adenoviruses) or genetically engineered viruses.

(f) Size-Separating the Microbubbles

A plurality of microbubbles prepared by the method of the invention may be separated according to diameter (size). The microbubble preparation may be separated according to diameter by differential buoyancy or by centrifugation. Immediately after the microbubbles are produced, a buffer may be added to the microbubble preparation to dilute the microbubbles to facilitate size separation. After adding the buffer, the vessel typically is covered with a paraffin film or other suitable cap, and the microbubble preparation is mixed with the buffer by gently inverting the vessel several times. The buffer used may be phosphate buffered saline (PBS), citrate buffer, succinate buffer, malate buffer, or any number of organic or inorganic buffers. The buffer pH may be in the range of about 2 to about 8. In one embodiment, a buffer with a pH of about 7.4 may be used when there is no desire to affect the size-stability, shelf life, and/or acoustic properties of the microbubbles. In another embodiment, the buffer pH may be in the range of about 6.5 to about 7.0 when the intent is to increase the microbubbles' shelf life without significantly altering their acoustic properties. In still another embodiment, the buffer may be in the range of about 2 to about 6 when the intent is to increase microbubble shelf life and modify their acoustic properties. In a preferred embodiment, 10 ml of buffer will be added to a microbubble preparation that was made using 16 ml of a gas-saturated, protein-saccharide solution.

After adding the buffer and mixing it with the microbubble preparation, the diluted microbubble preparation may be drawn into a syringe. Excess air may be expelled from the syringe. The syringe may be laid on its side. Larger diameter microbubbles may rise to form a milky-white band along the uppermost portion of the inner surface of the horizontal syringe barrel. After the larger microbubbles have risen to the upper, inner surface of the horizontal syringe, the syringe may be tilted at an angle in order to concentrate the risen, larger diameter microbubbles into a tighter band closer to the inner tip of the syringe plunger. The syringe may be tilted up at a 45° angle. After this tighter, more concentrated band of larger microbubbles has formed, the syringe may be placed in a vertical position (plunger up and expulsion orifice down) so that the larger microbubbles rise and are adjacent to the plastic or rubber stopper at the end of the plunger, and the smaller microbubbles are suspended in the mixed solution below the larger microbubbles. The smaller diameter microbubbles may be expelled from the syringe separately from the larger diameter microbubbles by depressing the syringe plunger until the mixed solution containing the smaller microbubbles is expelled from the syringe (into one or more fractions) and all that remains in the syringe is a milky white band comprised of the larger diameter microbubbles. A sample from each fraction, including the band retained in the syringe, may be examined with a microscope to determine the microbubble size distribution in each. This separation step may be repeated with each of the fractions (sometimes fractions may be combined or diluted further with buffer) as often as necessary so that the initial microbubble preparation is separated into fractions with specific size ranges.

The size fractions may range from about 0.35 μm to about 0.65 μm, about 0.8 μm to about 1.2 μm, about 1.5 μm to about 2.5 μm, about 2 μm to about 4 μm in diameter, etc. The range of microbubble diameters within each fraction, and the mean microbubble diameter within each may be adjusted to desired specifications by careful and repeated application of this separation procedure. Microscopic observation may be used to confirm that each separated fraction contains microbubbles with the desired mean diameter and diameter range. This may also be accomplished using a cell counter device. The cell counter device may be a Coulter Counter. If the microbubbles in a given fraction do not meet the desired size specifications, the separation procedure may be repeated on that fraction of microbubbles until a separated fraction with the desired size specifications is obtained. Fractions with the same mean microbubble diameter and diameter range may be combined to produce larger volumes of pooled microbubbles with the same size characteristics. The separated microbubbles may be stored in syringes suspended in solution. The solution may be a mixed protein and saccharide solution. The solution may be less than 6% of the volume. All air may be expelled from the syringe. The end of the syringe may be closed with a cap.

The microbubble preparation also may be separated by centrifugation. Longer centrifugation times will be required for larger volume preparations. The microbubble preparation may be centrifuged at between 800 rpm and 2,000 rpm, or between 1,200 rpm and 1,800 rpm. The microbubble preparation may be centrifuged at 1,500 rpm. The length of time for centrifuging the microbubble preparation may be dependent on the volumes to be centrifuged. A 1.5 ml volume containment vessel may be centrifuged for between 2 minutes and 20 minutes, between 5 minutes and 15 minutes, or between 7 and 12 minutes. A 0.5 ml volume tube may be spun for between 1 minute and 5 minutes. Centrifugation at higher speeds may result in microbubbles larger than 2.0 μm being lysed. Whole microbubbles of less than 1 μm may rise to the top of the tube. Careful application of the centrifugation procedure may be used to prepare microbubble preparations with mean diameters anywhere from 0.2 μm to 1.0 μm, with a variance as small as 2% and any larger variance.

(II) Microbubbles

The microbubbles prepared by the method of the invention comprise a gaseous interior that is surrounded by a shell comprised of a protein and a saccharide.

(a) Size

In general, the microbubbles may have diameters that range from about 0.3 μm to about 10.0 μm. In preferred embodiments, however, the microbubbles have narrow, defined size distribution (see FIG. 1). In one embodiment, the plurality of microbubbles may have a diameter of between 0.3 μm and 0.45 μm. In another embodiment, the plurality of microbubbles may have a diameter of between 0.3 μm and 1 μm. In a further embodiment, the plurality of microbubbles may have a diameter of between 0.9 μm and 1.1 μm. In an alternate embodiment, the plurality of microbubbles may have a diameter of between 1.8 μm and 2.2 μm. In still another embodiment, the plurality of microbubbles may have a diameter of between 2.7 μm and 3.3 μm. In a further embodiment, the plurality of microbubbles may have a diameter of between 3.6 μm and 4.4 μm. In another embodiment, the plurality of microbubbles may have a diameter of between 4.5 μm and 5.5 μm. Those of skill in the art appreciate that a large number of various size distributions is possible using the methods of the invention.

The method of making microbubbles may be adjusted to produce microbubble preparations with a wider or narrower range of microbubble diameters. Microbubble preparations may be further separated based upon their diameter (size) via the herein described separation methods. Measured amounts of microbubble preparations with different narrower, more defined ranges of diameters may be mixed together to produce a microbubble preparation containing a well-defined mixture of microbubbles. For example, a preparation containing microbubbles with a mean diameter of 4.0 μm+/−0.5 μm may be mixed 1:1 (volume to volume) with a preparation containing microbubbles with a mean diameter of 1.0 μm+/− 0.1 μm. Any combination of microbubble preparations that were separated into narrow, defined diameter preparations may be mixed together in any desired proportions to produce microbubble preparations with selected and known ranges of diameter, and then may be used for any of the applications mentioned below. A preparation with a selected mixture of microbubble diameters may be suitable for a specific application, while a preparation consisting of more uniformly, and narrowly sized microbubbles may be more suitable for other applications.

(b) Outer Shell and Inner Core

Microbubble preparation may be adjusted to produce microbubbles that have defined shell thickness. In general, the shell thickness of a microbubble may range from about 10 nm to about 1000 nm. In various embodiments, the shell thickness may be between 10 nm and 20 nm, between 20 nm and 30 nm, between 30 nm and 40 nm, between 40 nm and 50 nm, between 50 nm and 60 nm, between 60 nm and 70 nm, between 70 nm and 80 nm, between 80 nm and 90 nm, or between 90 nm and 1000 nm. In general, the thickness and composition of the shell affects the strength and elasticity of the shell, which in turn affects the stability and acoustic properties of the microbubble.

The inner core of the microbubble comprises a gas. In general, the interior volume of the microbubble may comprise from about 1% gas to about 100% gas. In certain embodiments, the microbubble may have an interior volume that is between 10% gas and 20% gas, between 20% gas and 30% gas, between 30% gas and 40% gas, between 40% gas and 50% gas, between 50% gas and 60% gas, between 60% gas and 70% gas, between 70% gas and 80% gas, between 80% gas and 90% gas, or between 90% gas and 100% gas.

(c) Acoustic Stability

The acoustic collapse threshold of the microbubbles produced by different preparation protocols can and will vary. In general, different microbubble preparations may have average, single microbubble, acoustic collapse thresholds between 0.3 MPa and 30 MPa. In one embodiment, the microbubble may exhibit an acoustic collapse threshold of less than 30 MPa. In another embodiment, the microbubble may exhibit an acoustic collapse threshold of between 0.3 MPa and 30 MPa. In a further embodiment, the microbubble may exhibit an acoustic collapse threshold of between 0.3 MPa and 10 MPa. In still another embodiment, the microbubble may exhibit an acoustic collapse threshold of between 0.5 MPa and 5 MPa. In an alternate embodiment, the microbubble may exhibit an acoustic collapse threshold of between 0.2 MPa and 0.8 MPa, 0.3 MPa and 0.9 MPa, 0.4 MPa and 0.8 MPa, 0.5 MPa and 0.7 MPa, 1 MP and 2 MPa, 2 MPa and 3 MPa, 3 MPa and 5 MPa, 5 MPa and 10 MPa, 10 MPa and 15 MPa, 15 MPa and 20 MPa, 20 MPa and 25 MPa, or 25 MPa and 30 MPa. The microbubble within a preparation may exhibit a deviation of between 1% and 15%, between 3% and 11%, between 3% and 5%, between 5% and 8%, or between 5% and 10% from the average collapse threshold for the microbubbles within a given preparation.

(d) Size Stability

The stability of the microbubbles to remain the same size can and will vary, depending upon the size of the microbubble and/or the strength of its shell. Typically, microbubbles tend to shrink in diameter over time. In general, microbubbles with an average diameter of about 1 micron are substantially size stable and exhibit no change in size for up to three years at room temperature or at 5° C. Microbubbles with average diameters of 2, 3, 4, or 5-6 microns generally are less size stable. In general, preparations of larger microbubbles may be size stable if no more than about 5% to about 25% of the preparation changes in size by no more than about 15% over about three days at 5° C. In some embodiments, about 1%, 2%, 5%, 10%, 15%, 20%, or 25% of the preparation may decrease in size about 5%, 10%, or 15%. Size stability may be estimated by determining the size transition time point (STT) as detailed in Example 5. Size stability may be improved about 5-10 fold by treating the microbubbles with an acidic buffer, as detailed above in (I)(d).

(e) Storage

The microbubble preparations may be stored at a temperature that ranges from about −100° C. to about 50° C. In various embodiments, the microbubbles may be stored between −80° C. and −20° C., between −20° C. and 0° C., between 0° C. and 5° C., between 3° C. and 5° C., between 0° C. and 25° C., between 20° C. and 25° C., or at room temperature.

The microbubbles may be stored in the protein-saccharide solution in which they were prepared, a similar protein-saccharide solution, or PBS at pH 7.4. For example, the microbubbles may be stored as a concentrated suspension in a minimum volume of the protein-saccharide solution, e.g. where the protein-saccharide solution comprises from about 1% to about 6% of the microbubble suspension volume. Alternatively, the microbubbles may be dehydrated and stored in a dried form. For this, the microbubble preparation may be dried at a temperature greater than 20° C., at room temperature, between 25° C. and 50° C., or at 37° C. Dehydrated, or dried preparations may be rehydrated by adding an appropriate amount of water to the storage barrel, tube, or container.

The microbubble preparations may be stored in a syringe barrel, microfuge tube, plastic container, polypropylene tube or container, or glass container. The storage vessel may be a Leur lock syringe. Excess protein-saccharide solution may be expelled after the microbubbles have risen in the syringe to form a concentrated band abutting the stopper of the plunger, when the syringe is in a vertical position (plunger up, Leur lock end down) and the Leur lock is sealed with a Leur lock cap. The microbubbles may rupture due to excess pressure if the syringe plunger is depressed after attaching the Leur lock cap. In a preferred embodiment, the microbubbles are rinsed with PBS buffer at pH 7.4, permitted to rise and concentrate in this buffer within a syringe, and are then stored as a concentrated suspension of microbubbles in the syringe after the excess PBS is expelled.

The microbubble preparations may be stored for days, weeks, months, or years. In general, the microbubbles remain stable for longer periods of time when stored at lower temperatures. The term "stable" as used herein means that the size and acoustic properties of the microbubble do not substantially change and the microbubbles do not exhibit signs of degradation. In general, the microbubbles of the invention may be stable for up to two years when stored at room temperature, or for as long or longer when stored at 3-5° C. In general, microbubbles with diameters of about 0.3-1 µm may be stable for at least one year when stored at room temperature; microbubbles with diameters between about 1 µm and 2 µm may be stable for at least six weeks when stored at room temperature; microbubble with diameters between 2 µm and 4 µm may be stable for at least one month when stored at room temperature; and microbubbles with diameters between 3 µm and 6 µm may be stable for up to about 2-4 weeks when stored at room temperature. In various embodiments, therefore, the microbubbles may be stable for at least one day, at least three days, at least one week, at least two weeks, at least one month, at least three months, at least six months, at least one year, or at least two years at room temperature. In general, the microbubbles remain stable for longer periods of time when stored at 3-5° C. For example, microbubbles of all sizes may be stable for up to two years when stored at 5° C.

The in vivo half-life of the microbubbles can and will vary depending upon the physical properties of the microbubble as well as the intensity of the insonating ultrasonic field.

(III) Applications

The microbubble, or an aggregate thereof, may be useful in a variety of medical applications. In one embodiment, the microbubbles may be used as contrast agents for ultrasonic imaging. In particular, microbubbles with diameters less than 1 µm and/or those with collapse thresholds greater than 10 MPa may serve as contrast agents with longer in vivo half-lives. Furthermore, the microbubbles may comprise a biological agent for targeting to a specific tissue for imaging. Alternatively, the microbubbles may be used for detecting ischemic and/or diseased tissue via ultrasound, by serving as an acoustic imaging contrast agent.

In another embodiments, the microbubbles may be used in applications that utilize the cavitation properties of the microbubbles. The particular microbubble chosen for a particular application will vary depending upon the desired acoustic properties of the microbubble. For example, microbubbles of different sizes may cavitate more energetically at a given frequency of ultrasound. Furthermore, variations in the thickness or strength of the shell may determine whether a microbubble cavitates stably or inertially. Non-limiting examples of suitable applications include thrombolysis, sonoporation, and targeted drug delivery. For example, the microbubble may enhance ultrasonic thrombolysis by transducing ultrasonic energy into shock waves, microstreaming, and harmonics to help disrupt thrombi and clots. Additionally, tissue plasminogen activator (tPA) may be attached to the microbubble to enhance the thrombolytic activity.

In further embodiments, the microbubbles may be used to enhance ultrasonic tissue ablation. For example, the microbubbles may be used in the ultrasonic ablation of tumors. However, the microbubbles also may be used to treat such conditions as endometriosis, macular degeneration, cataracts, secondary cataracts, calcium deposits, restenosis, atherosclerosis, atherosclerotic atheromas, infection, and the like.

In still another embodiment, the microbubble may be used to sonoporate cells or to promote delivery of pharmaceutically active agents or other therapeutics via sonophoresis. Sonophoresis may deliver drugs transdermally, into interstitial spaces, across blood vessels, or across the blood brain barrier.

In general, a method of treating a subject with microbubbles comprises administering the desired microbubbles to the subject and applying ultrasound energy to the subject.

(a) Administering the Microbubbles

The stored microbubble preparations may be drawn from the storage container. In some embodiments, the preparation may need to be created within seconds of injection by a device located near the place of its clinical application. In other embodiments, the microbubble preparation may be stable in storage for prolonged periods of time, and may be able to be withdrawn and directly injected without further alterations of the preparation.

The microbubble preparation may be administered orally, parenterally, sublingually, transdermally, rectally, transmucosally, topically, via inhalation, via buccal administration, or combinations thereof. Parenteral administration may be intravenous, intraarterial, intraperitoneal, subcutaneous, intramuscular, intrathecal, or intraarticular. The microbubble preparation may injected into a peripheral or central vein or artery at a desired amount per kg body weight, or alternatively, the microbubble preparation may be continuously infused. Alternatively, the microbubble preparation may be directly injected into a tissue, a tumor, or other structure (e.g., to serve as an ultrasonic imaging agent). In still another embodiment, the microbubble preparation may be administered in the form of an implant, which allows slow release of the agent.

The volume of the microbubble preparation to be administered may depend on a variety of factors including, the method of administration, the gas percentage of the microbubble suspension, the age, sex, weight, blood pressure, systemic venous return, pulmonary vascular resistance, and physical condition of the subject. Treatment may be initiated at small dosages, which can then be incrementally increased until the desired effect is achieved. The microbubble compositions may be administered in an amount from 0.01 ml/kg of body weight to about 40 ml/kg of body weight. An administered microbubble may contain more than one biological agent or microbubbles containing different biological agents may be co-administered.

Typically the subject will be a mammal. In various embodiments, the subject may be a human, a companion animal such as a cat or a dog, a show animal such as a horse, or a farm animal such as a cow, pig, or sheep.

(b) Applying Ultrasound Energy

Stable oscillation (stable cavitation) or collapse (inertial cavitation) of the microbubbles may be carried out by applying ultrasound of a certain frequency and/or intensity to the region of the subject where microbubble-mediated therapy is desired, after the microbubbles have been administered to or have otherwise reached that region. Lower and higher frequency ultrasound may be combined and applied to a region of interest. Ultrasound therapy may induce thrombolysis via the application of different frequencies from two or more transducers. Furthermore, frequencies may be mixed to provide alternating high and low frequency ultrasound. When acoustic or ultrasonic energy is applied at a frequency corresponding to the peak resonant frequency of the gas-filled microbubbles, the microbubbles may oscillate stably or collapse/rupture and release their contents, depending upon the intensity of the applied ultrasound. Acoustic or ultrasonic energy may also be applied at an off peak resonant frequency to achieve stable oscillation of the microbubble or induce collapse/rupture. Acoustic or ultrasound energy may be utilized not only to rupture the microbubble, but also to cause thermal effects that may increase the rate of the chemical cleavage and the release of an active drug from a prodrug.

Acoustic cavitation activity may be short-lived and end in a violent, energetic, and destructive collapse of the microbubbles. This energetic collapse may be referred to as inertial cavitation. Alternatively, the cavitation activity may be stable and characterized by protracted oscillations of the microbubbles in response to the ultrasound or acoustic energy. The nature of the cavitation may depend on the frequency, intensity, and other parameters of the acoustic waves, or ultrasound, and the physical parameters of the microbubbles, such as diameter or acoustic collapse threshold. Ultrasound energy may be applied via a focused beam or an unfocused beam. Acoustic or ultrasonic energy may be used in conjunction with the microbubble to produce circulatory fluid flow. Circulatory fluid flow may occur in the vicinity of a vibrating microbubble that has been set into motion due to cavitation by acoustic or ultrasonic energy. This type of circulatory fluid flow may be referred to as microstreaming.

The peak resonant frequency may be determined either in vivo or in vitro, by exposing the microbubble to ultrasound, receiving the reflected resonant frequency signals and analyzing the spectrum of signals received to determine the peak, using conventional means. The peak, as so determined, may correspond to the peak resonant frequency. The peak resonant frequency may correspond to the fundamental frequency administered; the microbubble may oscillate at subharmonics and/or at higher harmonics.

The peak resonant frequency of the microbubble may vary depending on the outside diameter and, to some extent, the elasticity or flexibility of the microbubble, with the larger and more elastic or flexible microbubble having a lower resonant frequency than the smaller and less elastic or flexible microbubble.

The microbubble may also rupture when exposed to non-peak resonant frequency ultrasound in combination with a higher intensity (wattage) and duration (time). This higher energy, however, may result in increased heating, which may not be desirable. By adjusting the frequency of the energy to match the peak resonant frequency, the efficiency of rupture and biological agent release may be improved, appreciable tissue heating may not generally occur, and less overall energy may be required. The application of mixed frequency ultrasound, wherein the frequency of the ultrasound is alternated or changed during the course of application, may also be used for effective microbubble cavitation.

For diagnostic or therapeutic ultrasound, any of the various types of diagnostic ultrasound imaging devices may be employed in the practice of the invention, the particular type or model of the device may not be critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. The device may employ a resonant frequency (RF) spectral analyzer. The transducer probes may be applied externally or may be implanted. Ultrasound may be initiated at lower intensity and duration, and then intensity, time, and/or resonant frequency may be increased until the microbubble is visualized on ultrasound (for diagnostic ultrasound applications) or ruptures (for therapeutic ultrasound applications). Complex waveforms, e.g. triangular, may be used to deliver mixed frequency ultrasound using a single transducer; or, two or more frequencies (mixed in specified proportions) may be used to drive a single transducer or sonic horn.

DEFINITIONS

To facilitate understanding of the invention, several terms are defined below.

"Acoustic cavitation" as used herein refers to an oscillatory change in the diameter of the microbubble in response to changes in acoustic or ultrasonic energy. The oscillations may be short lived and end in a violent collapse or implosion of the microbubble during a contraction phase of its oscillations (inertial cavitation), and/or a stable oscillation of the microbubble size that continues while the acoustic field is present and ends shortly after the acoustic field is no longer present (stable cavitation). In most instances of stable cavitation, the microbubble is extant after the acoustic filed is no longer present.

"Sonophoresis" as used herein refers to a transient permeability of skin, blood vessels organs, and/or other tissues to drugs, biological molecules, and/or other substances caused by a local-regional response of microbubbles to ultrasound. Sonophoresis differs from sonoporation in that drugs, biologicals, etc. pass between cells and do not necessarily enter cells. Sonophoresis may be used for transcutaneous delivery of drugs and other therapeutics into connective tissues, muscle, blood vessels, etc.

"Sonoporation" as used herein refers to a transient membrane permeabilization of cells situated in the vicinity of microbubbles exposed to ultrasound. Sonoporation initiated within tissues may be used to move drugs, biologicals, and/or other therapeutics from the blood stream (following an intravenous or intra-arterial injection of microbubbles with a therapeutic) into organs, tissues, across the blood-brain barrier, into tumors, etc. Sonoporation may be used to promote dispersion of therapeutics from one location in a tissue to other parts, e.g., dissemination of a therapeutic throughout a muscle following intramuscular injection of microbubbles comprising a therapeutic agent.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Preliminary Microbubble Production Procedure

Albumin and dextrose solutions were prepared in various tubes by mixing albumin and dextrose stock solutions in the appropriate amounts/ratios to achieve the desired concentrations. Tubing from a decafluorobutane gas tank was placed into the tube containing the mixed albumin-dextrose solution such that the tubing was at least 5 mm above the level of the liquid. The gas valve was turned slowly to the open position and gas was allowed to flow into the vessel for 4-6 seconds for 15-ml (17×100 mm) tubes or 5-9 seconds for modified polypropylene 50-ml tubes. Because the decafluorobutane gas is denser than air, gaseous "density" waves can be seen exiting the container as gas overflows the tube. This observation was used to confirm that the container had been filled with the added gas. A cap was placed on the tube and the tube was vortexed for 1 minute to 2 minutes on the highest setting. Vortexing may be stopped to add more gas and then resumed. This "stop and go" approach of adding more gas may be utilized several times to increase the content of dissolved gas. Alternatively, the gas may be continuously infused into the sealed container during the vortexing procedure. Making sure that the liquid splays out as a thin film across the inner surface of the vessel and that very little to no foam forms during vortexing helps maximize the amount of gas that gets dissolved into the mixed albumin-dextrose solution. The solution became slightly opaque as the gas was dissolved into it. Opacity of the liquid may be increased without foaming by halting and restarting the vortexing several times during the process. Foaming was also decreased by reducing the speed of the vortexer, but this may also reduce the amount of gas dissolved in the mixed albumin-dextrose solution.

The cap was removed from the tube and the appropriate sized sonic horn was inserted into the tube. A 1.1 cm diameter sonic horn was used in 13-15 ml tubes and a 1.9 cm diameter sonic horn was used in 40-50 ml tubes. A Fisher model 500 sonicator was used to produce the microbubbles. The maximal power output was 500 W at a sinusoidal frequency of 20 kHz. The location of the sonic horn's tip relative to the surface of the mixed albumin-dextrose solution was varied to produce microbubbles of different sizes and with different acoustic properties. The sonic horn tip was positioned about 1-4 mm above the liquid surface and a single, 1 minute sonication exposure at 60% to 100% of the maximum power output was used to produce microbubbles with an average diameter of between 0.3 µm to 1.0 µm. Increasing the distance of the horn tip above the liquid surface and increasing the sonication power produced microbubbles with smaller diameters. However, if the sonic horn was located more than about 5 mm above the liquid surface, then sufficient sound energy to produce microbubbles could not be transmitted to the liquid, and there was a risk of damaging the sonic horn and/or the sonic generator. Touching the horn to the liquid produced microbubbles with larger diameters while locating the horn above the liquid surface produced smaller diameter microbubbles.

A two-step sonication procedure was used to produce the most stable (longer lasting) microbubbles with average diameters of 2.0 µm and larger. The first sonication step (30 sec to 1 min long at 125-300 W) was performed with the tip of the sonic horn immersed into the mixed albumin-dextrose solution. A greater depth of immersion of the sonic horn tip (up to half the distance from the surface of the liquid to the bottom of the tube/vessel) resulted in microbubbles with a larger average diameter. The second sonication step (30 sec to 1 min long at 200-450 W) was made with the tip of the sonic horn 1-3 mm above the liquid surface. The vessel containing the microbubble-forming solution was flushed with gas (e.g. perfluorocarbon gas) prior to administering the second sonication step.

It has been observed that using more than two sonication steps can produce microbubbles with desired properties that cannot be produced with just two sonication steps, e.g., microbubbles with average single microbubble collapse thresholds greater than 15-20 MPa. The vessel containing the microbubble-forming solution was always flushed with gas (e.g. perfluorocarbon gas) prior to administering any sonication step following the first sonication.

Immediately after sonication, a buffer (e.g., PBS, pH 7.4) was added and the microbubbles were mixed. Microbubbles and bubbles larger than 10 µm were allowed to rise above the surface of the liquid for about 3-10 minutes. The upper layer of foam (larger coarse bubbles) was removed by aspiration. Aspiration was ceased when the layer of foam appeared to resemble shaving cream, wherein individual bubbles cannot be distinguished. The solution was then drawn into an appropriately sized syringe and subjected to centrifugation and/or other size separation strategies to further separate the microbubbles into fractions with different, average diameters. The microbubbles were examined under a microscope to confirm the average diameter of the microbubbles in each separated fraction.

Preparation of 2 µm to 4 µm Diameter Microbubbles.

A 5% (w/v) albumin stock solution was mixed with a 15% (w/v) dextrose stock solution in a volume-to-volume ratio of 1:2 for a total of 6.0 ml in a 17×100 mm tube. After mixing in decafluorobutane gas via vortexing, the first acoustic exposure was performed at a power setting of 150 W for 30 seconds using a 1.1 cm diameter sonic horn. The sonic horn was attached to a 20 KHz sonic disrupter (Fisher Model 500 Sonicator). The tip of the sonic horn was placed ~2.0 cm below the surface of the solution for administering the first acoustic pressure. The tip of the sonic horn was placed ~1.5 mm above the solution surface for administering the second acoustic pressure, which was delivered for 25 seconds at a power level of 300 W. This procedure yielded a mixture of microbubble diameters that was weighted toward 2-4 µm diameter.

A specific example for making 3.0 µm diameter microbubbles follows. The microbubble formation solution was made by mixing 5% albumin stock solution with a 15% dextrose stock solution in a volume-to-volume ratio of 1:2 for a total volume of 16 ml in a modified 50-ml centrifuge tube. After mixing in the decafluorobutane gas using a vortexer (setting of ¾th of maximum to minimize foam production for this larger volume prep), the first acoustic exposure was performed at a power setting of 250 W for 30 seconds and the second acoustic exposure at a power setting of 450 W for 20 seconds. A 1.9 cm sonic horn was attached to 20 kHz sonic disrupter (Fisher Model 500 Sonicator) and used for both exposures. The tip of the sonic horn was placed ~2.0 cm below the surface of the solution for administering the first acoustic pressure. The tip of the sonic horn was placed ~1.5 mm above the solution surface for administering the second acoustic pressure. This protocol produced a large quantity of microbubbles with the predominant microbubble size being 3.0 µm.

The preceding microbubble preparations each had an average acoustic collapse threshold of approximately 0.6 MPa at 3 MHz. The average acoustic collapse threshold of the microbubbles was increased by increasing the duration of the first acoustic exposure, with a maximum attainable average acoustic collapse threshold greater than 7-10 MPa. However, if the first acoustic exposure duration was increased too much, the average acoustic collapse threshold of the microbubbles decreased markedly.

Preparation of 5 µm to 6 µm Diameter Microbubbles.

A 15% (w/v) albumin solution was mixed with a 15% (w/v) dextrose solution in a volume-to-volume ratio of 1:2 for a total volume of 6.0 ml in a 17×100 mm tube. After mixing in the decafluorobutane gas, the solution was treated with two different acoustic exposures using a 1.1 cm sonic horn that was attached to a 20 KHz sonic disrupter (Fisher Model 500 Sonicator). The first acoustic exposure was performed at a power setting of 150 W for 40 seconds with the tip of the sonic horn placed ~2.0 cm below the surface of the solution. The second acoustic exposure was administered at a power setting of 300 W for 25 seconds with the tip of the sonic horn placed ~1.5 mm above the solution surface. The majority of the microbubbles produced using this protocol had diameters between 5 µm and 6 µm with very few microbubbles smaller than 4.0 µm in diameter.

A larger volume of 5-6 µm diameter microbubbles was prepared by mixing a 15% albumin stock solution with a 15% dextrose stock solution in a volume-to-volume ratio of 1:2 for a total volume of 16 ml in a modified 50 ml centrifuge tube. After mixing in the decafluorobutane gas, the first acoustic exposure was administered at a power setting of 300 W for 25 seconds and the second acoustic exposure was administered at a power setting of 200 W for 30 seconds. A 1.9 cm sonic horn was attached to 20 KHz sonic disrupter (Fisher Model 500 Sonicator) and used for both exposures. The tip of the sonic horn was placed ~2.0 cm below the surface of the solution for administering the first acoustic pressure. The tip of the sonic horn was placed ~1.0 mm above the solution surface for administering the second acoustic pressure. This procedure yielded a mixture of microbubble diameters that was weighted towards 5 to 6 µm diameter microbubbles.

The microbubble preparation protocols could be adjusted slightly so that the average single microbubble collapse threshold at 3 MHz was in the range of 0.2 MPa to 12.0 MPa. The average single microbubble collapse threshold was changed by adjusting the duration of the first sonication step. Reducing the duration of the first sonication step decreased the average single microbubble collapse threshold, while increasing the duration of the first sonication step increased the average single microbubble collapse threshold. However, increasing the duration of the first sonication step too much may cause the average single microbubble collapse threshold to decrease markedly.

Preparation of 1.0 μm Diameter Microbubbles.

For the preparation of 1.0 μm microbubbles, a 5% albumin solution was mixed with a 5% dextrose solution in a volume-to-volume ratio of 1:3 for a total volume of 6.0 ml in a 17×100 mm tube. After mixing in decafluorobutane gas, acoustic pressure was administered using a power setting of 300-350 W for 50 seconds to 75 seconds using a 1.1 cm diameter sonic horn, with the tip of the acoustic horn located 1 mm above the surface of the liquid.

A larger volume of microbubbles was prepared by mixing a 5% albumin solution with a 5% dextrose stock solution in a volume-to-volume ratio of 1:3 for a total volume of 16.0 ml in a modified 50-ml centrifuge tube. After mixing in decafluorobutane gas, acoustic exposure was administered using a 1.9 cm sonic horn (tip of the horn 2 mm above the liquid surface) at a power setting of 450 W for 80 seconds.

The steps in preparing microbubbles according to this example may be adjusted slightly so that the average single microbubble collapse threshold at 1 MHz was in the range of 0.7 MPa to 20.0 MPa. Dissolving more decafluorobutane gas into the mixed albumin-dextrose solution and/or using a higher acoustic pressure increased the average single microbubble collapse threshold, while doing the opposite decreased the average single microbubble collapse threshold.

Preparation of 0.3-1.0 μm or 1.0-1.5 μm Diameter Microbubbles.

The first protocol (i.e., 6 ml) detailed above for the preparation of 1.0 μm diameter microbubbles was repeated except that the acoustic power and the duration of the sonication were increased by 20-30% to produce microbubbles with an average diameter of 0.3 to 1.0 μm. Alternatively, the acoustic power and the duration of the sonication were decreased by 20-30% to produce microbubbles with an average diameter of 1.0 to 1.5 μm.

A 5% albumin solution was mixed with a 5% dextrose stock solution in a volume-to-volume ratio of 1:3 for a total volume of 16.0 ml in a modified 50 ml centrifuge tube. After mixing in decafluorobutane gas, acoustic exposure was administered using a 1.9 cm sonic horn at a power setting of 450 W for 45 seconds. This procedure produced microbubbles with an average diameter of 0.5 μm.

Example 2

Optimized Protocols for Microbubble Production

The protocols for producing microbubbles having narrow size distributions and distinct acoustic properties were further refined and optimized. Table 1 lists the parameters for one-step and two-step sonication protocols to produce preparations whose predominate microbubble diameter was 1.0 μm, 2.0 μm, 3.0 μm, 4.0 μm, or 5.0-6.0 μm. All of these protocols involved sonication with a Fisher Model 500 W sonic dismembrator (20 KHz) using a 1.9 cm sonic horn and a combined serum albumin and dextrose solution volume of 16 ml.

TABLE 1

Microbubble Production Protocols.

| Microbubble Diameter | | Serum Albumin Solution | Dextrose Solution | Sonication Step 1 | Sonication Step 2 |
|---|---|---|---|---|---|
| 1.0 μm | A | 4 ml 5% | 12 ml 5% | 450 W 70-80 sec | None |
|  | B | 4 ml 5% | 12 ml 5% | 150 W 20-30 sec | 400-450 W 70 sec |
| 2.0 μm | A | 4 ml 5% | 12 ml 5% | 125 W 30 sec | 375 W 45 sec |
|  | B | 4 ml 15% | 12 ml 15% | 250 W 25 sec | 300 W 20 sec |
| 3.0 μm | A | 5.3 ml 5% | 10.7 ml 15% | 250 W 30 sec | 450 W 20 sec |
|  | B | 5.3 ml 15% | 10.7 ml 15% | 250 W 30 sec | 450 W 20 sec |
|  | C | 5.3 ml 15% | 10.7 ml 15% | 250 W 40 sec | 450 W 30 sec |
| 4.0 μm | A | 4 ml 5% | 12 ml 5% | 250 W 30 sec | 350 W 40 sec |
|  | B | 5.3 ml 15% | 10.7 ml 15% | 300 W 25 sec | 250 W 40 sec |
| 5-6 μm | A | 4 ml 5% | 12 ml 5% | 250 W 35 sec | 250 W 45 sec |
|  | B | 5.3 ml 15% | 10.7 ml 15% | 300 W 25 sec | 200 W 30 sec |

The serum albumin used was bovine serum albumin (BSA) (catalog no. A7906; Sigma-Aldrich, St. Louis, Mo.). Identical results were obtained using human serum albumin (HSA) purchased from Talecris Biotherapeutics, Inc. (Research Triangle Park, N.C.) under the trade name Plasbumin-25, which comes as a sterile, 50% solution (w/V). This was diluted with sterile 18 MΩ water to make stock solutions containing 5%, 10%, 15%, or 20% HSA (w/v). Other bovine serum albumin (BSA) and human serum albumin (HSA) preparations from the same suppliers (BSA-Sigma; HSA-Talecris Biotherapeutics, Inc) have been used to produce microbubble successfully. Serum albumins from pigs, rabbits, and rats have also been used successfully. However, the protocol parameters in Table 1 need to be adjusted slightly and systematically in order to achieve comparable results, putatively to compensate for differences in the chemical nature of each different serum albumin preparation (see below).

The serum albumin and dextrose solutions were added to a 50 ml polypropylene centrifuge tube with a plug seal cap (Corning #430290) and the two solutions were mixed gently by inverting the capped tube several times. The tube was uncapped and then the open end of a piece of tubing, connected to the decafluorobutane gas tank was inserted into the tube and held in a position just above the surface of the serum albumin and dextrose solution. The gas flow was started and used at a rate where the flowing gas just made a discernable dimple in the liquid surface. Gassing was continued for 5-7 seconds, with several seconds of decafluorobutane gas overflow from the centrifuge tube (flow of the denser decafluorobutane was clearly visible as a shimmering in the air near the tube opening) indicating that the centrifuge tube was flooded with the gas.

After stopping the gas flow the centrifuge tube was capped and placed onto a vortex mixer operating at 75% to full speed and the gas was mixed into the solution for at least one minute. After one minute of vortexing, the solution was examined to ensure that it had a translucent opaque appearance, indicating gas saturation. If the solution was not saturated, vortexing was continued for at least another 30 sec. Sometimes re-flooding the tube with decafluorobutane before continuing the vortexing was necessary to achieve the desired endpoint of a gas-saturated solution. Optimal mixing was attained when the solution was splayed in a thin layer across the inner surface of the tube, and could be facilitated by stopping and starting the vortexing several times. Foaming of the solution was unavoidable; however, the best results with microbubbles production were obtained when foaming was kept to a minimum.

One Step Protocols.

Immediately after vortexing, the gas-saturated albumin-dextrose solution was transferred to a 40 ml Beckman ultracentrifuge tube (thin wall). The volume above the solution was quickly purged with decafluorobutane gas, the sonic horn was inserted so that it either just touched the surface of the liquid or was 1-2 mm above it, and the sonication step was performed using the specified power setting and duration.

Two Step Protocols.

The first sonication step was performed in a polystyrene blood cell counter vial used for Coulter and other cell counters (35 ml capacity). The shape and material of the vial have proven best for this step. The gas-treated mixture was poured into the vial and the tip of the sonic horn was immersed into the mixture and positioned at the midpoint of the liquid volume (roughly at the 10 ml mark on the vial, due to the displacement of the horn). The sonicator was turned on for the prescribed time and the sonic horn was maintained at the same position throughout this step. This sonication step produces a high pitched noise, and some operators have found it necessary to wear disposable, foam earplugs. Additionally, the liquid mixture becomes hot during this sonication step and so the vial should be held near the top by hand (insulating glove optional) or with a holder.

The solution turned milky white either during the first sonication step or shortly thereafter. After this change, the tube contents were transferred to either a 40 ml ultracentrifuge tube or a cut-down 50 ml polypropylene tube (cut to 45 ml). The tube was purged with decafluorobutane gas, the sonic horn was inserted so that it either just touched the surface of the liquid or was 1-2 mm above it, and the second sonication was performed using the prescribed power setting and duration.

Production of 1 µm Diameter Microbubbles.

The most common, effective and reproducible procedure for making a uniform preparation of 1 µm diameter microbubbles was the 1.0 µm protocol A in Table 1. A photomicrograph of a sample preparation of microbubbles with an average diameter of 1.0 µm is shown in FIG. 1A. To prepare microbubbles smaller than 1 µm in diameter, the albumin and dextrose solutions were either kept ice cold before they were mixed together or, if they were used at room temperature, the sonication intensity was increased to 500 W and the ultrasound was delivered in two to three successive 30 sec bursts with a 20-30 sec pause between bursts.

One micrometer microbubbles that are more resistant to ultrasonic collapse (more acoustically stable) may be produced by increasing the final concentration of the serum albumin, the dextrose, or both (up to 6% serum albumin and 10% dextrose); and then using the one step sonication of 1.0 µm protocol A (Table 1) to form the microbubbles. Alternatively, the same mixture of 5% serum albumin and 5% dextrose may be subjected to a two-step sonication treatment (i.e., protocol B in Table 1).

Both of these procedures produced 1 µM diameter microbubbles, but there was an increasing proportion of stable, larger diameter microbubbles as the concentration of serum albumin and/or dextrose was increased, or when the two stage sonication protocol was employed. These larger microbubbles were generally removed using the separation protocols described below.

Although 1.0 µM diameter microbubbles were produced in almost all preparation protocols, the single sonication step protocols using low serum albumin concentrations (1% to 2% final concentration) gave high yields of 1.0 µM diameter microbubbles. The resultant microbubbles did not require size separation after the initial extraction step because any larger microbubbles present either separated out rapidly due to their greater buoyancy or lysed shortly thereafter because their shells were weak and unstable. Size separation (see below) had to be used for isolating 1.0 µM diameter microbubbles from preparations made with higher serum albumin levels or made using two sonication steps because the larger diameter microbubbles were now more stable and longer lasting. However, obtaining pure samples of 1.0 µm diameter microbubbles was still relatively easy because the larger microbubbles were much more buoyant and faster rising and were soon partitioned from the smaller 1.0 µM diameter microbubbles.

Production of 2 µm or Large Diameter Microbubbles.

The most reproducible protocols for producing 2 µm diameter and larger microbubbles utilized the two-step sonication protocols in Table 1. Photomicrographs of different preparations are presented in FIG. 1B-E. Microbubbles with diameters larger than 1.0 µM may be produced using the one-step sonication procedure, but these have proven to be weaker with respect to sonic disruption and have a shorter shelf life, viz. not longer than 2 weeks. The simplest adaptation to obtain a one-step sonication procedure for making larger diameter microbubbles was to adjust the 1.0 µM protocol A (Table 1) by increasing the concentration of the albumin stock solution from 5% to 7.5-15%.

Microbubbles with diameters in the range of 2.0 µM to 3.0 µM were the most difficult to produce, size separate, and were less stable than the 1 µM microbubbles with regard to maintaining their size and acoustic properties during protracted storage at 5.0° C. Protocol adjustments were also more substantial in order to retain size stability and acoustic performance when the lot of serum albumin and or decafluorobutane gas was changed. Microbubbles in the range of 4-7 µM in diameter were the easiest to size separate (due to fast rising) and were surprisingly stable with respect to size and acoustic performance throughout storage.

Example 3

Sonicator Power Test

There is evidence that the power output from one Fisher Model 500 sonicator can vary significantly from that of another when the same power setting is entered into the control panel for both machines. Such variability between sonicators could make it very difficult to successfully produce microbubbles using the sonicator power settings listed in Table 1. Additionally, some investigators will have other sonicator types and models that they wish to use for making microbubbles, and there will likely be an even greater discrepancy between the power outputs of these devices compared to that from the model 500 sonicator used to develop the protocols in Table 1.

Hence, it is recommended highly that every investigator subject their sonicator to the power output test described below. If the test results differ significantly from those obtained with the model 500 sonicator used to develop the protocols in Table 1, an investigator should adjust the power setting on their sonicator to match the power output results of the sonicator used to design the protocols in Table 1, otherwise the expected results will not be obtained. The sonicator power test detailed below may be performed using either a 1.1 cm diameter sonic horn or a 1.9 cm diameter sonic horn. The results with either horn will validate the performance of the sonicator with the other horn, and any fractional power setting adjustments indicated by the test results using one horn may be applied successfully to the sonicator when the other horn is used.

1.1 cm Diameter Sonic Horn.

Several 17×100 mm polystyrene culture tubes were each filled with 6.66 g (6 ml: specific gravity is 1.11 g/ml) of Dow Corning Silicone Fluid (oil) 710. Weighing was more accurate than aliquoting the oil volumetrically since the oil is very viscous. The tubes were capped and placed in a 25° C. water bath for at least 5 min. Each measurement was made by taking one tube from the water bath, inserting the 1.1 cm sonic horn into the tube so that the horn tip was 4 cm from the bottom of the tube (position on the tube pre-marked), and turning on the sonicator at a specified power setting for 5 sec. After removing the sonic horn the tube was capped, the oil was mixed by gentle inversion (2-3 times) and then the oil temperature was measured by inserting the tip of a 0.35 mm diameter thermocouple 9.0 mm (position pre-marked) below the surface of the oil. This process was repeated three times for each power setting.

1.9 cm Diameter Sonic Horn.

The test was performed by adding 17.76 g (16 ml) of DOW Fluid 710 to a polystyrene blood cell counting vial (35 ml capacity). The remainder of the procedure was identical to that described above for the 1.1 cm diameter sonic horn.

Results.

Figure 2:
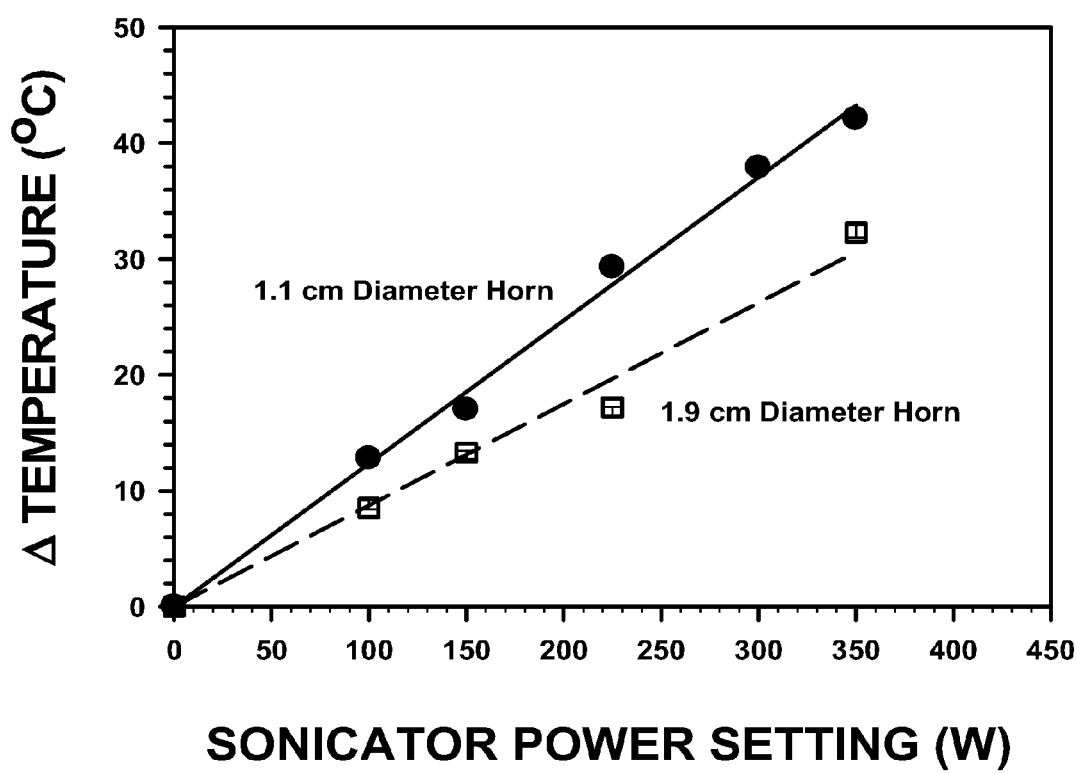
FIG. 2 illustrates a method for calibrating sonicators. Silicone Oil was used as an acoustic absorber and the temperature increase induced by a 5 sec sonication is plotted as a function of the power level that the sonicator was set during the sonication. Ultrasonic energy (20 KHz) was delivered by a 1.1 cm or a 1.9 cm diameter sonic horn attached to a Fisher Model 500 sonicator. Each data point represents the mean value of three temperature measurements. The error bars representing the standard deviation of the three measurements are smaller than the data symbols, as can be seen in the open square symbols.

FIG. 2 presents the change in temperature as a function of the sonicator power setting. The temperature rise was different for the two horns because a larger volume of oil was used for testing the 1.9 cm diameter sonic horn. These results may be used to calibrate any sonicator such that it delivers the same power as indicated in Table 1.

A Temperature Increase vs. Power Setting curve like that shown in FIG. 2 must be produced for every sonicator that will be used to produce microbubbles. For a given sonicator, if the slope of the resultant linear relationship (it is always linear) between temperature rise and power setting is identical to that in FIG. 2 then that sonicator can be used to produce microbubbles using the same power settings for all of the microbubble protocols listed herein, i.e. the sonicator to be used and the one used for acquiring the data in FIG. 2 have the same power output for the same power setting. However, if the slope of the linear relationship between temperature rise and power setting for a given sonicator (slope=S2) differs from the slope of the line seen in FIG. 2 (slope=S1), then the power settings for a given sonicator have be adjusted by the scale factor of S1/S2 for each of the sonication power settings listed for every microbubble protocol presented herein in order to produce microbubbles of comparable size distribution and acoustic properties.

Example 4

Size Fractionation of Microbubble Preparations

All microbubble preparations generally were subjected to some degree of size fractionation, even if it was to just separate microbubbles from the foam and very large microbubbles (10 μm diameter and greater) that were also produced during the sonication steps. After the final sonication step for each preparation, the microbubble preparation tubes were placed upright in a rack, 10 ml of room temperature, pH 7.4 phosphate buffered saline (PBS) was added to each tube, the tube was sealed with paraffin film, inverted gently several times to mix the foam and PBS to extract trapped microbubbles, and then returned to the rack so that the foam and larger microbubbles rose to reveal a liquid fraction.

A 20 ml plastic, Luer-lock syringe fitted with a blunted 1½ inch long 18 g needle (sharp tip cut off and smoothed) was inserted slowly and carefully into the tube (no foam overflow) so that the needle touched the bottom of the tube. The lower fraction (liquid microbubble suspension) was drawn slowly into the syringe without taking up any foam, and a small sample of this extracted suspension was examined with a microscope to determine its microbubble size distribution. All air bubbles were removed from the syringe by orienting the syringe vertically (i.e., tip up) and tapping it against the benchtop (or other solid surface) to help dislodge bubbles adhering to the plunger and syringe walls and direct them to the syringe tip. Once all air bubbles were expelled the syringe tip was sealed with a Luer-lock syringe cap. The cap well was pre-filled with PBS and an adherent drop of microbubble suspension was expelled from the syringe so that air would not be introduced into the syringe when these two components were mixed during capping.

The foam remaining in the tube was re-extracted, as above, and after the foam and larger bubbles had clearly separated from the milky liquid microbubble suspension, the latter was drawn into a 10 ml or 20 ml syringe and a small sample was examined with a microscope. Depending upon the microbubble protocol used and the size of the microbubbles sought, the foam may be extracted one more time to yield useful, albeit larger diameter microbubbles. The nature and number of subsequent fractionation steps depended upon the protocol used to produce the microbubbles and the size(s) of the microbubbles that were isolated.

1.0 μm Diameter Microbubble Preparations.

For 1.0 μm microbubble preparations made with a single sonication step, the syringes containing the extracted microbubble suspensions were capped and immediately stored upright (plunger up) in racks, at 5° C. Any larger microbubbles either dissipated or rose to the top of the syringe within 1 to 6 h (depending on their size) and formed a distinctly white band. The lower, milky fraction was collected by ejecting it slowly from the syringe tip, taking care not to eject any of the upper fraction. If the band of larger microbubbles was substantial, it was extracted with 5-10 ml of PBS to determine if any usable microbubbles were contained therein.

At this point, a sample of both microbubble fractions was examined with a microscope to determine if size separation was successful (e.g. 90% or more of the microbubbles in the lower fraction are 1 μm) or if further fractionation was required, (e.g. the lower fraction had too many microbubbles larger or smaller than 1 μm, and/or the upper fraction contained a significant amount of 1 μm microbubbles that could be recovered). When making 1 μm microbubbles using two sonication steps (and in some one step formulations), it was found that a significant proportion of the microbubbles (20% or more) in the initial, extracted suspension can be larger than 1.0 µm. When this occurred, size fractionation was more effective when performed according to the scheme described below for isolating microbubbles larger than 1.0 µm.

2.0 µm and Larger Diameter Microbubble Preparations.

Syringes containing the liquid microbubble suspensions were placed horizontally on a bench top so that the larger microbubbles rose more quickly and formed a distinctly white band along the top half of the syringe barrel. Once this white band formed (7-20 min, depending on the microbubble size distribution) and did not get observably larger over a 3-5 min span, the syringe was raised to a 45° angle from the vertical (plunger up) until the white band rose to the rubber plunger head (tapping syringe barrel aided this process), after which the syringe was positioned vertically in a rack so that the upper fraction spread out across the plunger head. The lower, more gray appearing fraction of microbubbles was expelled gently from the syringe into two separate sub-fractions of essentially equal volume, and the upper fraction (whiter band) was re-extracted with 5-10 ml of PBS. Samples of all three fractions were then examined with a microscope to determine the distribution of microbubble sizes within each.

In almost all instances, further fractionation of the initial microbubble fractions was required to yield final microbubble preparations wherein 90% or more of the microbubbles had diameters that were within 10% of a specified mean diameter, e.g. 3 µm±0.3 µm. This simply involved reapplication of the fractionation procedures already described.

Size Distribution.

Figure 3A:
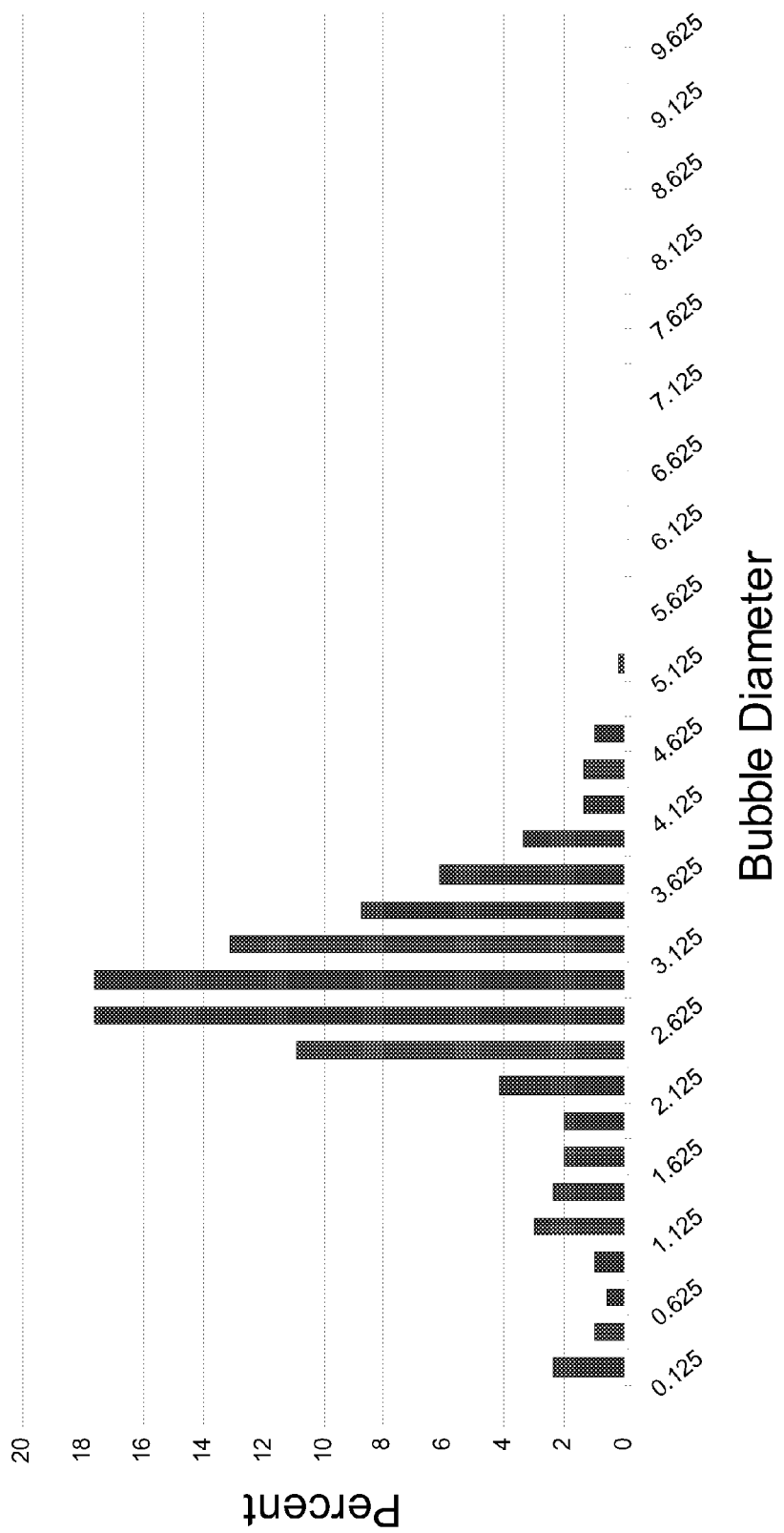
FIGS. 3A and 3B show the size distribution of two preparations of microbubbles with an average size of 2.96 µm (FIG. 3A) or 3.53 µm (FIG. 3B).
Figure 3B:
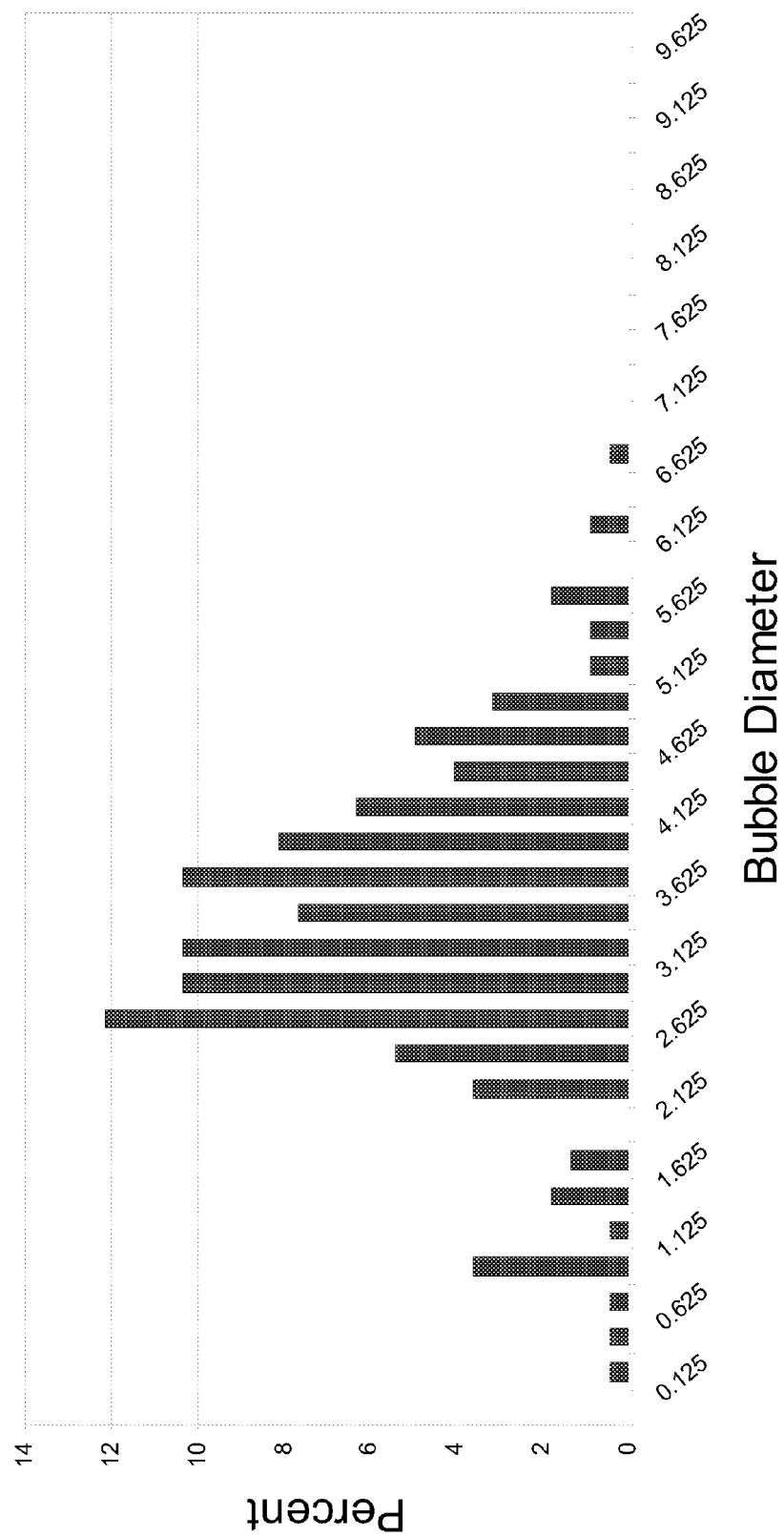

The size distribution of the microbubbles in several preparations was determined (see FIG. 3). The preparation presented in FIG. 3A had an average diameter of 2.96 µm, and about 70% of the microbubbles had a diameter within about 10% of the mean. The preparation presented in FIG. 3B had an average diameter of 3.53 µm, and about 60% of the microbubbles had a diameter within about 15% of the mean.

Example 5

Size Stability

The majority of 1.0 µM diameter microbubbles were very size-stable, and most 1.0 µM microbubble preparations exhibited no change in size even when they were maintained at an air-liquid interface for several days. Microbubbles began to degas and shrink at an air-liquid interface, and those with weaker shells did so more quickly. Hence, the time that microbubbles in a preparation remain at an air-liquid interface before showing signs of shrinkage is a characteristic of the microbubbles made using a specific protocol, and is one benchmark that may be used to determine whether a new batch of microbubbles may perform identically to one made earlier with the same protocol. Size stability assessment works for all microbubbles with a diameter of 2.0 µM and larger.

A 50-75 µl aliquot of a microbubble preparation was placed onto a glass slide and spread out (using a pipette tip etc.) to form a flattened film rather than a rounded droplet (better for phase contrast microscopy). Microbubbles rose to the surface of the liquid within 0.5 to 1.3 min after which they were imaged and photographed. Phase contrast was optimal but not essential. The microbubbles were observed as a function of time after they were placed on the glass slide, and the length of time required for a significant reduction in the diameter (15-20%) of at least 15% of the microbubbles to be observed was recorded and noted at the size transition time point (STT).

The STT measurement varied slightly from one observer to another, but was a reliable benchmark for assessing microbubble size stability and a 15-20% change in the STT was a good indicator that new preparations made with a given protocol would perform differently than those in earlier preparations made with the same protocol. If 25-50% of the microbubbles exhibit shrinkage of 30-150% in diameter in less than 5 min, then that preparation will not retain their diameter for more than 2-5 days when stored concentrated at 5° C. If microbubble size remained constant throughout three days of storage at 5° C., then there was a better than 97% probability that size would remain constant for 20 days.

Example 6

Microbubble Response to Ultrasonic Insonation

Three tests were developed to confirm that a microbubble preparation's acoustic properties were consistent with those of earlier preparations that were prepared and tested identically. This was done to establish measurable benchmarks to ensure consistency of ultrasonic performance for successive microbubble preparations.

One test measured the fraction of microbubbles that remained intact following exposure to a continuous wave (CW) ultrasonic field. A second test measured the threshold pulse wave (PW) intensity (fixed duty cycle) that completely destroyed a constant flow rate, microbubble stream immediately after it traveled a fixed distance through the ultrasonic field. The third test involved insonating a chamber pre-filled with a set number of microbubbles and through which a constant stream of additional microbubbles (of the same type) was flowing. The measured endpoint was the lowest PW intensity that destroyed all of the microbubbles within the chamber within a specified time period. This last test provided an indication of how well the microbubbles shielded each other from the disruptive effects of the ultrasound. Although none of these tests makes an absolute measurement of microbubble collapse threshold, they do provide measurable, comparative benchmarks that can be used to ensure consistency of microbubble production and performance from one preparation to the next.

Each acoustic test was performed in tanks filled with degassed water using inexpensive ultrasound diathermy units (models 716 and 730; Mettler Electronics Corp., Anaheim, Calif.), or a more expensive system comprising an arbitrary function generator (model AFG3102; Tektronix Inc., Richardson, Tex.), a 50 dB RF power amplifier, and a digital oscilloscope. Surprisingly, both ultrasound systems yielded similar numerical results for each test and performed equally well with regard to providing benchmark measurements to ensure reproducible performance from new microbubble preparations in experiments and other applications.

CW Test for Microbubble Durability (Duration Test).

The microbubble stock was diluted with PBS to a specified concentration (1 AU, 2-3 µm bubble≈$2.86 \times 10^7$ bubbles/ml measured by $OD_{530}$) for the microbubble being tested, and 600 µl of this microbubble suspension was placed into a 32 mm long, cylindrical, clear, Mylar chamber made from a Mylar drinking straw (5.7 mm O.D. and 5.22 mm I.D). This chamber was fitted with a cap constructed from two 8-10 mm long pieces of silicone tubing (positioned concentrically) and silicone sealant. The only constraints for the tubing were that the outer tubing had an O.D. of 5.2 mm and that the inner tubing had an I.D. of 1.7 mm. The 1.7 mm lumen of the inner tubing served as a pressure release port so that the microbubbles were not subjected to a positive pressure that could rupture them when the chamber was capped. The hole was small enough so that the viscosity of the microbubble suspension prevented microbubbles from leaking out and water from leaking into the chamber. The Mylar chamber was attached to a holder that positioned it horizontally within the exposure tank so that it was in the center of the ultrasound field, 6.5 cm from the transducer face.

The chamber was irradiated with a 1 MHz sinusoidal CW ultrasound (intensity depending upon microbubble and preparation parameters) for 20 sec. Afterwards, the amount of remaining microbubbles was measured ($OD_{530}$) and the fraction of microbubbles remaining was recorded. Although the 20 sec exposure time proved sufficiently long for the test, longer exposures were used for selected microbubble preparations to determine the time constant for microbubble decay as a function of exposure time.

Unshielded Microbubble Destruction Threshold.

The concentrated microbubble stock suspension was diluted with PBS to a specified concentration (measured by $OD_{530}$) for the microbubble being tested (e.g. for testing 3 μm diameter bubbles, a 4-fold dilution of the running solution measured 1 AU at 530 nm and contained≈$1.14 \times 10^8$ bubbles/ml) and 5-10 ml of the solution was placed into a supply chamber, atop a layer of silicone oil (DOW Corning 510). The supply chamber was insulated with acoustic absorbing material to protect microbubbles from any impinging ultrasound. The outlet of the supply chamber was 1.55 mm in diameter and this was connected to a 3.5 cm long piece of Mylar straw filled with PBS, which served as the insonation chamber for the microbubbles.

A syringe pump was used to pump the silicone oil into the lower end of the supply chamber at a constant rate of 0.5 ml/min to drive a stream of microbubbles into the insonation chamber. Once the microbubble stream had traveled 5 mm the ultrasound was turned on (PW, 20% duty cycle) and the intensity was increased until no microbubbles survived to travel further than the 5 mm distance.

Shielded Microbubble Destruction Threshold.

The setup for this test was identical to that for the unshielded destruction threshold test except that the exposure chamber was prefilled with a specified concentration of microbubbles. Insonation was started immediately after the stream of microbubbles began to enter the exposure chamber. The measurable endpoint was the minimum PW intensity that destroyed all microbubbles within the insonation chamber in 15 seconds. Following each test with a selected PW intensity, the chamber was emptied, re-filled with microbubbles, and the test was run again with a new PW intensity. This procedure was repeated until the sought endpoint was achieved.

Results.

Table 2 lists the acoustic performance for some of the microbubbles produced using the protocols in Table 1 when subjected to the acoustic tests. These data illustrate that several factors affected the measured endpoints for each microbubble preparation. The most influential factor on microbubble performance was diameter, with the smaller diameter microbubbles being more resistant to ultrasonic lysis at both 1 MHz and 3 MHz.

Data in Table 2 also demonstrate that microbubbles having the same diameter but made using different protocols exhibited different acoustic properties. The general trends were that increasing the concentration of serum albumin, the sonication power level (first and/or second sonication), and/or the duration of the sonications increased microbubble stability when exposed to ultrasound while decreasing each of the parameters had the converse effect.

The endpoints for each microbubble preparation were similar when the tests were performed with either the Mettler Diathermy Units or with the same transducer driven with amplified sinusoidal waves. The ultrasonic output of the latter setup was adjusted to reproduce the CW and Pulse Wave (20% duty cycle train: 2 msec on 8 msec off per pulse) of the Mettler Units, except for a fixed amplitude, 40 msec duration timing pulse that occurred in one second intervals (present in every Mettler Unit: 4 tested). The intensity within this 40 msec pulse was fixed but varied from one Mettler Unit to the other (0.5-0.8 W/cm²) and in the absence of the 20% duty cycle pulses this 40 msec pulse noticeably agitated the microbubbles upon impact, once every second. As Table 2 illustrates, the timing pulse alone was capable of lysing some of the 3.0 μm diameter microbubble preparations during the shielded and unshielded destruction threshold assays when the ultrasound frequency was 1.0 MHz.

TABLE 2

Acoustic Properties.

| | Duration: 1 MHz, 0.1 W/cm², 20 s (M716) | Shielded Destructive Threshold 3 MHz (M730) | Unshielded Destructive Threshold 3 MHz (M730) | Shielded Destructive Threshold 1 MHz (M730) | Unshielded Destructive Threshold 1 MHz (M730) | Shielded Destructive Threshold 3 MHz (Tektronic AFG 3102) | Unshielded Destructive Threshold 3 MHz (Tektronic AFG 3102) | Shielded Destructive Threshold 1 MHz (Tektronic AFG 3102) | Unshielded Destructive Threshold 1 MHz (Tektronic AFG 3102) |
|---|---|---|---|---|---|---|---|---|---|
| 1 um Bubble A | 51% remaining (1 MHz, 1.0 W/cm², 20 s) | Unable to complete this test | Unable to complete this test | Unable to complete this test | Unable to complete this test | Unable to complete this test | Unable to complete this test | Unable to complete this test | Unable to complete this test |
| 3 um Bubble A | 34-37% | 0.6 W/cm² | 0.2 W/cm² | 0.0 W/cm² Timing pulse sufficient | 0.0 W/cm² Timing pulse sufficient | 0.5 W/cm² | 0.2 W/cm² | 0.2 W/cm² | 0.1 W/cm² |
| 3 um Bubble B | 40-45% | 0.7 W/cm² | 0.4-0.5 W/cm² | 0.1 W/cm² Timing pulse sufficient | 0.0 W/cm² Timing pulse sufficient | 0.6 W/cm² | 0.3 W/cm² | 0.3 W/cm² | 0.2 W/cm² |
| 3 um Bubble C | 49-55% | 0.8-0.9 W/cm² | 0.6-0.7 W/cm² | 0.2 W/cm² | 0.1 W/cm² | 0.7 W/cm² | 0.4 W/cm² | 0.4 W/cm² | 0.2 W/cm² |

Example 7 pH Curing and Hardening of Microbubbles

Microbubble size stability, storage duration, and acoustic durability may also be adjusted by treating microbubbles with citrate buffers at pH levels in the range of 3.0-7.0, with greater changes in size stability and acoustic resistance being achieved with the lower pH buffers. Microbubbles may be treated immediately after they are produced, while they are being size separated, after size separation, or anytime in between. The magnitude of the pH-induced changes in microbubble size stability and acoustic durability decreased as the time between microbubble production and pH treatment increased, regardless of the pH used.

Treatment during size separation was accomplished by performing the first extraction in a lower pH citrate buffer and keeping the microbubbles in this buffer throughout size separation. The microbubbles were transferred to PBS at pH 7.4 by performing the final size separation step in a larger volume of pH 7.4 PBS (to dilute out the lower pH PBS) or adding a predetermined amount of higher pH PBS so that the final pH was adjusted to 7.4. The latter approach was more efficient. Lower pH treatment following size separation was accomplished by diluting the microbubbles in the lower pH citrate buffer, keeping them suspended in this buffer for at least 5 min, and then size separating the microbubbles with two large volume rinses of pH 7.4 PBS.

The extraction and size separation procedures for a microbubble preparation were delayed accordingly in order to apply the lower pH citrate at a given time after microbubble production. The microbubble preparation was agitated periodically (every 2-3 min) to prevent or inhibit size separation. At the appropriate time following production, the microbubbles were extracted with the lower pH citrate buffer and size separation was then performed.

Results.

Figure 4:
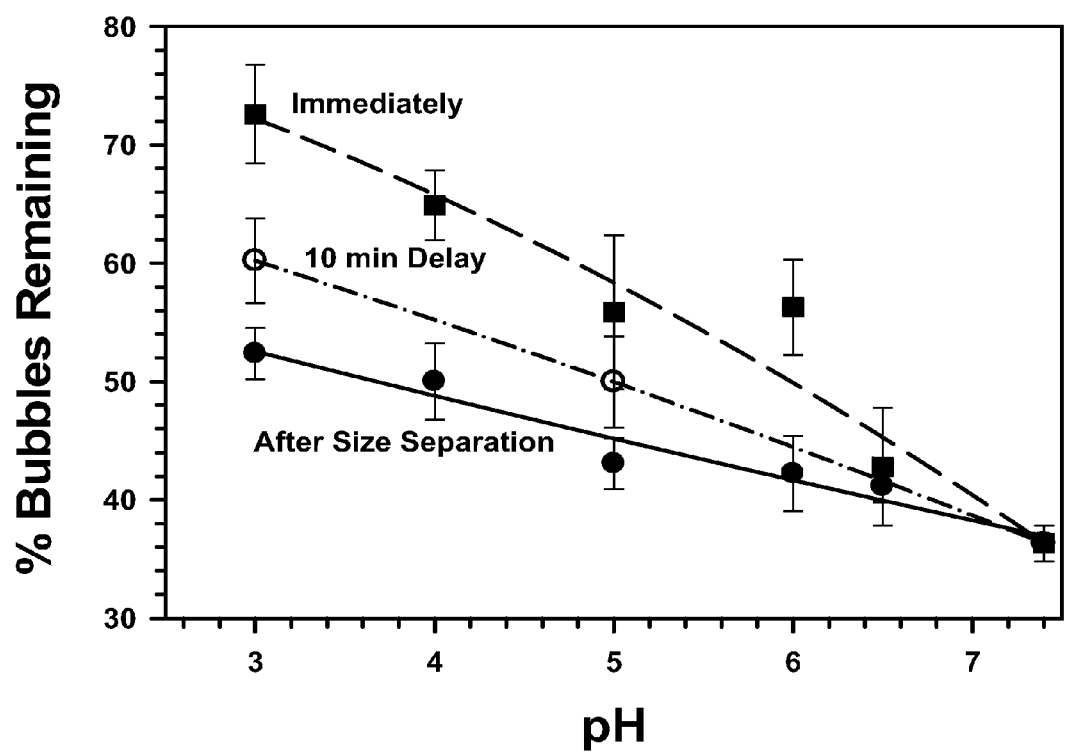
FIG. 4 illustrates how the acoustic properties (resistance to acoustic lysis) of microbubbles may be modified by treating the microbubbles with citrate buffer, as a function of the citrate buffer pH. This figure shows the percent of an initial sample of 3.0 µm diameter microbubbles preparation (i.e., protocol A, Table A) that remained intact following a 20 second exposure to continuous wave 1.0 MHz ultrasound at an intensity of 0.1 W/cm$^2$. The microbubbles were treated with citrate buffer immediately following microbubble production, 10 min after microbubble production, or after size separation. Each data point represents at least three separate measurements.

Treating microbubbles with citrate buffers at pH levels in the range of 3.0 to 7.0 proved to be another means of stabilizing microbubbles and increasing their resistance to ultrasonic lysis. FIG. 4 illustrates how microbubble stability changed, as measured by the durability, following treatment with citrate buffers, as a function of the buffer pH. The preparation was 3 µm diameter microbubbles prepared according to protocol A in Table 1. After being rinsed with pH 7 PBS the microbubbles were subjected to the Duration Test (CW ultrasound at 1 MHz) to measure the effect of the citrate buffer treatment on microbubble acoustic durability. Treatment at lower pH levels increased the acoustic durability of the microbubbles regardless of when they were treated. FIG. 4 also illustrates that using lower pH citrate buffers to extract microbubbles from the initial preparation immediately following the sonication steps had a greater effect upon increasing microbubble stability against ultrasonic lysis than when microbubbles were treated after being size-separated. Treating microbubbles with citrate buffer at intermediate times following production had intermediate effects on their acoustic stability.

Experiments were performed in which the pH of the citrate buffer was adjusted to 7.4 at varying times after adding it to the microbubbles, using a sodium hydroxide solution. These experiments (data not shown) demonstrated that the full stabilizing effects of the citrate buffer took place within 5.0 min and did not change during longer treatment times, out to 40 min.

Preliminary experiments with succinate-based buffers produced results similar to those obtained with citrate buffers. However, phosphate buffers had little or no effect on the acoustic stability of the microbubbles (data not shown). It was found, however, that treating microbubbles with phosphate buffered saline at pH 3 or 4 markedly increased the size stability and storage time for the treated microbubbles by up to four-fold. Preliminary experiments involving treatment of microbubbles using buffers with pH levels higher than 8.0 indicated that this destabilized microbubbles and made them weaker with respect to ultrasonic lysis.

Example 8

Microbubble Storage

After the microbubbles have been size-separated, they were permitted to rise within a capped syringe to form a tight concentrated band (at room temperature or 5° C.). Once the microbubble band had formed, the syringe plunger was depressed to move the concentrated microbubble band to the bottom of the syringe while expelling almost all of the underlying PBS form the syringe. After capping the syringe it is stored vertically (plunger up) in a test tube rack at 5° C.

Microbubbles larger than 1.0 µm rose quickly and required only time (0.5-4 h) to form a concentrated band at the top of a syringe. Although some 1.0 µm diameter microbubble preparations also rose to the top of the syringe within 9-16 h, others rose much more slowly. Hence, centrifugation was used to hasten the rising of the latter.

The 1.0 µm diameter microbubbles were drawn up into a syringe which had the upper $3/4^{ths}$ of the plunger shaft cut off with a Dremmel tool, which permitted the syringe to be spun in a centrifuge with a swinging bucket rotor. (If a fixed angle rotor is available then there is no need to cut the syringe plunger.) The syringe with the microbubbles was spun at 800-1,200 rpm (110-250 rcf) for 12-25 min. After the microbubbles rose, the PBS was expelled and the concentrated microbubbles were stored as described above. When the plunger shaft was cut off, needle-nose pliers were used to move the cut plunger shaft up and down so that the band of concentrated microbubbles could be manipulated.

The microbubbles were stored at (1) room temperature (short term storage—a few days to several weeks for microbubble preparations with average diameters larger than 1 µm and more than a year for microbubbles with diameters of 1 µm or smaller; (2) 5° C. (longer storage—up to 2 years for all microbubble sizes; (3) −20° C., or at −80° C., up to 33% of microbubbles larger than 2 µm would shrink in size to a diameter of about 1 µm. Microbubble preparations having an average diameter of between 0.2 µm to 1 µm may be stored at room temperature for more than one year while exhibiting no signs of degradation.

For storage at −20° C. or −80° C., the freezing process was allowed to occur gradually by placing the syringe directly into the freezer. Rapid freezing in liquid nitrogen worked well for the 1.0 µm diameter and smaller microbubbles, but it caused the larger microbubbles to lyse. The 1.0 µm diameter and smaller microbubbles stored well at either −20° C. or −80° C. and appeared unaltered when thawed. Thawing was done by submersing the syringe in a water bath at room temperature, or by submersing the syringe in a 37° C. water bath.

Microbubbles were also stores in a dried state. For this, a concentrated microbubble suspension (in serum/dextrose solution) was placed onto a glass slide and the liquid was evaporated at room temperature. A second concentrated suspension was placed on a glass slide and the liquid was evaporated at 37° C. The microbubbles were stored for at least 6 months in this dried state. The dried microbubbles were rehydrated by adding water to the dehydrated microbubbles. The volume of water used was equal to the volume of the original microbubble suspension, pre-hydration.

Larger volumes of microbubbles were dried by placing concentrated microbubble suspensions (in serum/dextrose solution) into a test tubes and then placing the tubes on a rotation device (with the tubes rotating around the long axis) at room temperature or at 37° C. The tube was rotated until the bubble suspension was dehydrated. Rehydration was performed by adding the appropriate amount of water to the tubes and rotating the tubes on the rotation device until the microbubbles were rehydrated. The rehydrated microbubbles were still gas-filled, maintained their original size, and appear to have the same acoustic properties that they had prior to dehydration.

Example 9

Accounting for Variations in Serum Albumin Lots

Different lots of serum albumin sometimes exhibit different properties in response to the microbubble production protocols. This was successfully addressed by minor changes in the intensity settings on the sonication device used to produce the microbubbles.

In general, if microbubbles produced with a given protocol were smaller and/or weaker (shorter STT and lower destruction thresholds) when prepared with a new serum albumin lot, one or more of the following adjustments rectified the problem: 1) increasing the final serum albumin concentration by 5-10% (simplest and most usual fix), 2) increasing the power setting for the first sonication step by 10-40%, 3) decreasing the power setting by 10-30% for the second sonication step, and/or 4) increasing the duration of the first or second sonication step by 15-40%. The magnitude of the adjustment(s) had to be determined empirically but remained the same throughout the subsequent use of a given serum albumin lot. The converse adjustments must be made when microbubbles made with a new serum albumin lot were larger and/or stronger than those made with an earlier lot.

Weaker microbubbles resulting from a serum albumin lot change can also be strengthened by treating them with citrate buffer (pH 3.0 to 6.5) rather than by adjusting the production parameters.

Example 10

Collapse Data for 4 μm Microbubbles

Figure 5:
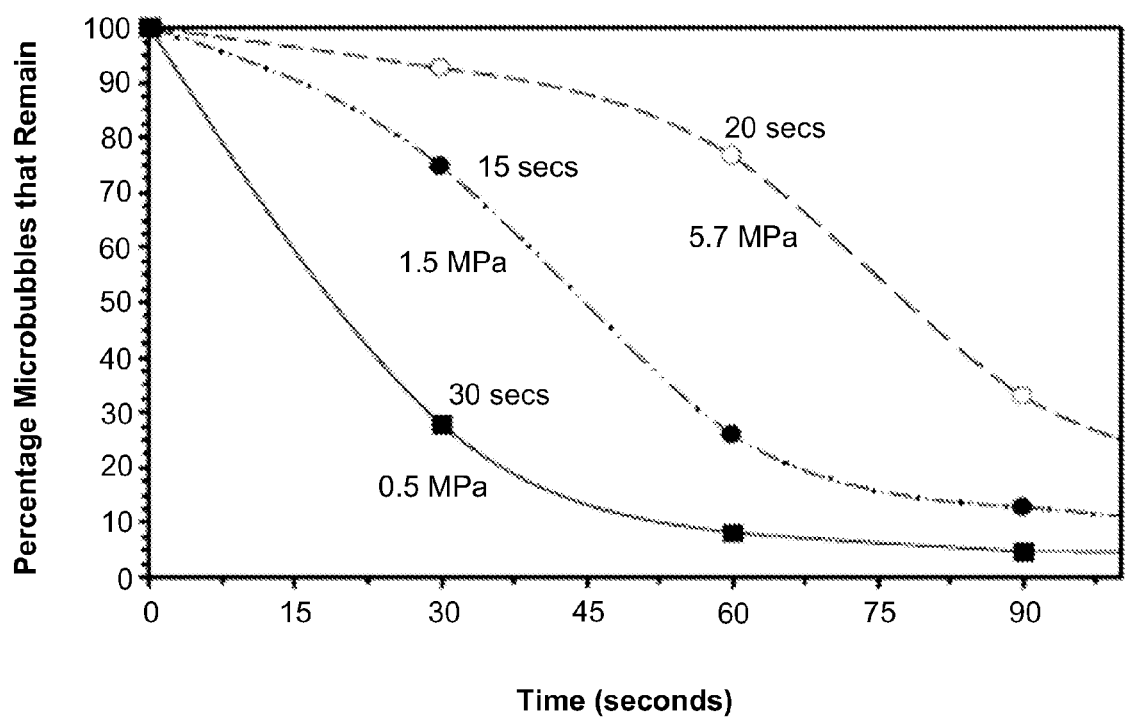
FIG. 5 presents acoustic lysis data for 4 µm microbubbles. Plotted is the percent of microbubbles remaining following exposure to 1 continuous wave 1.0 MHz ultrasound at an intensity of 0.1 W/cm$^2$ as a function of exposure time. The three different curves represent data from microbubble preparations made using the same two-step sonication process, except that the duration of the first round of sonication was varied. The average single microbubble collapse threshold value for each microbubble preparation is presented in mega Pascals (MPa), as detailed in Example 10.

Microbubbles were made by mixing 10% albumin and 15% dextrose solutions and using a two-stage sonication (20 KHz) procedure. The duration of the first, lower intensity sonication was changed (duration in seconds indicated by each curve in FIG. 5); all else remained constant. Microbubble collapse was first measured by measuring the decrease in microbubble concentration while they were insonated with 1 MHz ultrasound at 0.1 W/cm². These data illustrate how changing the parameters of the first sonication step altered the acoustic properties of identically sized microbubbles. The average single microbubble collapse threshold value was measured using a device designed by William D. O'Brien, Ph.D., University of Illinois, Urbana-Champaign. The single microbubble collapse threshold values for each microbubble preparation in FIG. 5 are listed in MPa. The figure also shows that a small increase in the duration of the first sonication step may eventually lead to reducing the single microbubble collapse threshold, ostensibly by overdenaturing the serum albumin or otherwise damaging the albumin and/or dextrose used to produce the microbubbles.

Example 11

Microbubble Induced Thrombolysis

Figure 6:
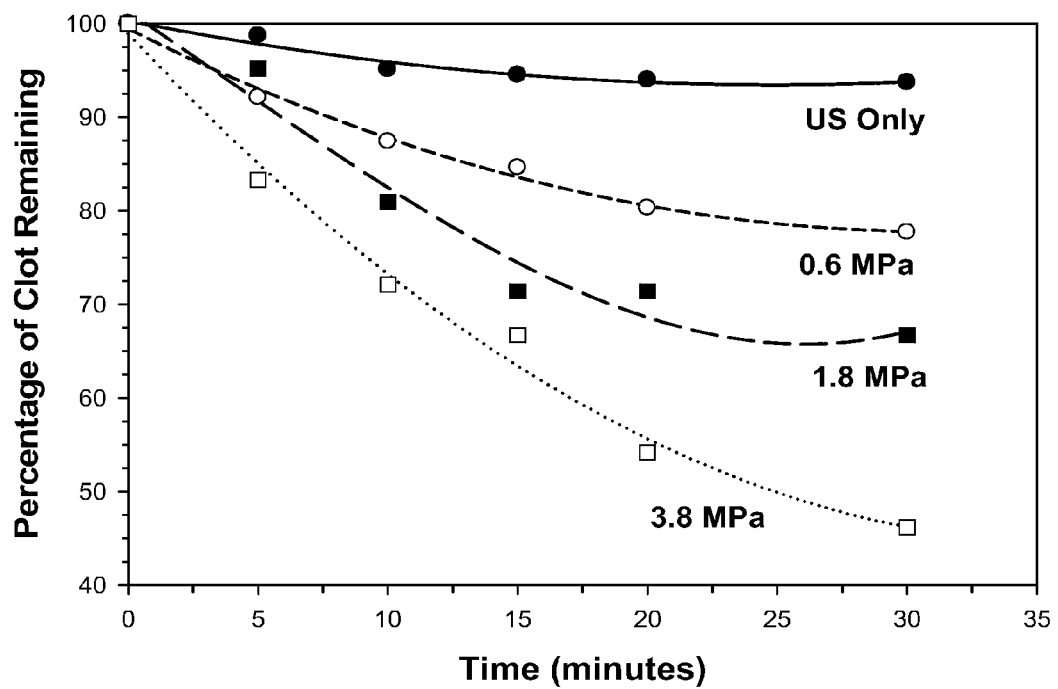
FIG. 6 illustrates microbubble-induced sonothrombolysis. Plotted is the percent of in vitro clot remaining as a function of time for clots exposed to ultrasound only (US), and microbubbles (MB) having different acoustic collapse thresholds.

Microbubble preparations (i.e., 3-4 μm diameter) were used for in vitro thrombolysis of clotted human blood. Thrombolysis efficacy was measured as the rate of clot dissolution by the action of the microbubbles and ultrasound, as measured by a loss in clot mass. See FIG. 6 (These data were obtained using an in vitro system for treating blood clots with microbubbles and ultrasound—1 MHz Ultrasound, continuous wave, 0.4 W/cm²). Ultrasound (US) caused very little change in the clot mass, but using microbubbles (MB) plus ultrasound increased thrombolysis markedly (microbubbles fed continuously into chamber). Thrombolysis was greater with microbubbles that had a higher collapse threshold (indicated by each curve in FIG. 6). A higher threshold may ostensibly mean a more energetic collapse to lyse clot more effectively; or the microbubbles just lasted longer under ultrasound.

What is claimed is:

1. A method for preparing a plurality of microbubbles filled with a perfluorocarbon gas, the plurality of microbubbles having an average, single microbubble acoustic collapse threshold of about 0.3-30 MPa, at least 80% of the microbubbles having diameters within about 10% of a selected mean diameter, the method comprising:
    (a) saturating a solution comprising serum albumin and dextrose with the perfluorocarbon gas; and
    (b1) delivering a first round of ultrasound energy at a power level of about 150 W within the solution and delivering a second round of ultrasound energy at a power level of about 400-450 W outside the solution, wherein the plurality of microbubbles has a mean diameter of about 1.0 micron;
    (b2) delivering a first round of ultrasound energy at a power level of about 125-250 W within the solution and delivering a second round of ultrasound energy at a power level of about 300-375 W outside the solution, wherein the plurality of microbubbles has a mean diameter of about 2.0 microns;
    (b3) delivering a first round of ultrasound energy at a power level of about 250 W within the solution and delivering a second round of ultrasound energy at a power level of about 450 W outside the solution, wherein the plurality of microbubbles has a mean diameter of about 3.0 microns;
    (b4) delivering a first round of ultrasound energy at a power level of about 250-300 W within the solution and delivering a second round of ultrasound energy at a power level of about 250-350 W outside the solution, wherein the plurality of microbubbles has a mean diameter of about 4.0 microns;
    (b5) delivering a first round of ultrasound energy at a power level of about 250-300 W within the solution and delivering a second round of ultrasound energy at a power level of about 200-250 W outside the solution, wherein the plurality of microbubbles has a mean diameter of about 5-6 microns; or
    (b6) delivering only one round of ultrasound energy at a power level of about 400-500 W outside the solution, wherein the plurality of microbubbles has a mean diameter of about 0.5-1.0 micron.

2. The method of claim 1, wherein the first round of ultrasound energy delivered in steps (b1), (b2), (b3), (b4), or (b5) is delivered by a sonic probe immersed and positioned at the midpoint of the solution volume; and the second round of ultrasound energy delivered in steps (b1), (b2), (b3), (b4), or (b5) or the one round of ultrasound energy delivered in step (b6) is delivered by a sonic probe that is positioned no more than about 3 mm above the surface of the solution.

3. The method of claim 1, wherein the solution in step (b1) comprises about 1-2% of serum albumin and about 3-4% of dextrose; the first round of energy is delivered for about 20-30 seconds; the second round of energy is delivered for about 70 seconds.

4. The method of claim 1, wherein the solution in step (b2) comprises about 1-2% of serum albumin and about 3-4% of dextrose; the first round of energy is about 125 W and is delivered for about 30 seconds; the second round of energy is about 375 W and is delivered for about 45 seconds.

5. The method of claim 1, wherein the solution in step (b2) comprises about 3-6% of serum albumin and about 9-12% of dextrose; the first round of energy is about 250 W and is delivered for about 25 seconds; the second round of energy is about 300 W and is delivered for about 20 seconds.

6. The method of claim 1, wherein the solution in step (b3) comprises about 1-6% of serum albumin and about 9-12% of dextrose; the first round of energy is delivered for about 30 seconds; the second round of energy is delivered for about 20 seconds.

7. The method of claim 1, wherein the solution in step (b3) comprises about 1-6% of serum albumin and about 9-12% of dextrose; the first round of energy is delivered for about 40 seconds; the second round of energy is delivered for about 30 seconds.

8. The method of claim 1, wherein the solution in step (b4) comprises about 1-2% of serum albumin and about 3-4% of dextrose; the first round of energy is about 250 W and is delivered for about 30 seconds; the second round of energy is about 350 W and is delivered for about 40 seconds.

9. The method of claim 1, wherein the solution in step (b4) comprises about 3-6% of serum albumin and about 9-12% of dextrose; the first round of energy is about 300 W and is delivered for about 25 seconds; the second round of energy is about 250 W and is delivered for about 40 seconds.

10. The method of claim 1, wherein the solution in step (b5) comprises about 1-2% of serum albumin and about 3-4% of dextrose; the first round of energy is about 250 W and is delivered for about 35 seconds; the second round of energy is about 250 W and is delivered for about 45 seconds.

11. The method of claim 1, wherein the solution in step (b5) comprises about 3-6% of serum albumin and about 9-12% of dextrose; the first round of energy is about 300 W and is delivered for about 25 seconds; the second round of energy is about 200 W and is delivered for about 30 seconds.

12. The method of claim 1, wherein the solution in step (b6) comprises about 1-2% of serum albumin and about 3-4% of dextrose, the power level is about 450 W, the energy is applied continuously for about 70-90 seconds, and the mean diameter of the plurality of microbubbles is about 1 micron.

13. The method of claim 1, wherein the solution in step (b6) comprises about 1-2% of serum albumin and about 3-4% of dextrose, the power level is about 500 W, the energy is applied discontinuously for about 70-90 seconds, and the mean diameter of the plurality of microbubbles is about 0.5 microns.

14. The method of claim 1, wherein the plurality of microbubbles has a size stability in which the mean diameter does not change more than about 10% for up to about two years at 5° C.

15. The method of claim 14, further comprising treating the plurality of microbubbles with a buffer having a pH of about 3 to about 6, wherein the size stability and the average, single microbubble acoustic collapse threshold of the plurality of microbubbles are increased.

16. The method of claim 1, wherein the plurality of microbubbles further comprises a biological agent selected from the group consisting of a contrast agent, a pharmaceutical agent, a prodrug, a protein, a peptide, an antibody, and a nucleic acid.

* * * * *